(12) United States Patent
Kuan et al.

(10) Patent No.: US 9,115,196 B2
(45) Date of Patent: Aug. 25, 2015

(54) ANTIBODIES AND IMMUNOTOXINS THAT TARGET HUMAN GLYCOPROTEIN NMB

(71) Applicants: THE UNITED STATES OF AMERICA AS REPRESENTED BY THE SECRETARY OF HEALTH, Rockville, MD (US); Duke University, Durham, NC (US)

(72) Inventors: Chien-Tsun Kuan, Cary, NC (US); Darell D. Bigner, Mebane, NC (US); Ira H. Pastan, Potomac, MD (US)

( * ) Notice: Subject to any disclaimer, the term of this patent is extended or adjusted under 35 U.S.C. 154(b) by 305 days.

(21) Appl. No.: 13/897,587

(22) Filed: May 20, 2013

(65) Prior Publication Data

US 2013/0245244 A1    Sep. 19, 2013

Related U.S. Application Data

(62) Division of application No. 13/276,012, filed on Oct. 18, 2011, now Pat. No. 8,445,216, which is a division of application No. 12/092,228, filed as application No. PCT/US2006/042735 on Oct. 31, 2006, now Pat. No. 8,039,593.

(60) Provisional application No. 60/732,227, filed on Oct. 31, 2005.

(51) Int. Cl.

| C07H 21/04 | (2006.01) |
|---|---|
| C07K 16/28 | (2006.01) |
| C12N 15/00 | (2006.01) |
| A61K 47/48 | (2006.01) |
| C07K 16/30 | (2006.01) |
| G01N 33/574 | (2006.01) |
| C07K 16/12 | (2006.01) |
| A61K 39/00 | (2006.01) |

(52) U.S. Cl.
CPC ........... *C07K 16/28* (2013.01); *A61K 47/48438* (2013.01); *C07K 16/1214* (2013.01); *C07K 16/30* (2013.01); *C12N 15/00* (2013.01); *G01N 33/57484* (2013.01); *A61K 2039/505* (2013.01); *C07K 2317/565* (2013.01)

(58) Field of Classification Search
None
See application file for complete search history.

(56) References Cited

FOREIGN PATENT DOCUMENTS

WO    2006/071441    7/2006

OTHER PUBLICATIONS

Kuan et al.: "GPNMB: A New Target for Human High-Grade Gliomas (HGL) Immunotherapy" Neuro-Oncology, [Online] vol. 7, No. 3, Jul. 2005, pp. 369-369, XP002420602.
Kam Fai Tse et al.: "CR011, a Potent Fully Human Monoclonal Antibody-Auristatin E Conjugated Prodrug Targeting Melanoma" Proceedings of the Annual Meeting of the American Association for Cancer Research, New York, NY, US, Apr. 16, 2005, XP002403962.
Tse Kam Fai et al.: "CR011, a Fully Human Monoclonal Antibody-Auristatin E Conjugate, for the Treatment of Melanoma" Clinical Cancer Research, The American Association for Cancer Research, US, vol. 12, No. 4, Feb. 15, 2006, pp. 1373-1382, XP002403963.
Kuan Chien-Tsun et al. : "Glycoprotein Nonmetastatic Melanoma Protein B, a Potential Molecular Therapeutic Target in Patients with Gliblastoma Mutliforme." Clinical Cancer Research: An Official Journal of the American Association for Cancer Research, vol. 12, No. 7, Pt. 1, Apr. 1, 2006, pp. 1970-1982, XP002420603.
Kuan C-T et al.: "Monoclonal Antibodies Recognizing Human GPNMBWT/GPNBSV React With Human High-Grade Gliomas (HGL)" Proceedings of the Annual Meeting of the American Association for Cancer Research, New York, NY, US, vol. 44, Jul. 2003, pp. 1116-1117. XP008070220.
Chen et al., Current Drug Delivery, 2004, 1 (4): 361-376.

*Primary Examiner* — Hong Sang
(74) *Attorney, Agent, or Firm* — Banner & Witcoff, Ltd.; Sarah A. Kagan

(57) ABSTRACT

The invention provides high affinity antibodies suitable for forming immunotoxins that inhibit the growth of cells expressing human glycoprotein NMB, including glioblastoma multiforme cells, anaplastic astrocytoma cells, anaplastic oligodendroglioma cells, oligodendroglioma cells, and melanoma cells. The antibodies may be formed in cells transformed with an isolated nucleic acid encoding a polypeptide comprising an antibody heavy chain variable region ("VH") and an antibody light chain variable region ("VL"). Such nucleic acids are provided.

9 Claims, 8 Drawing Sheets

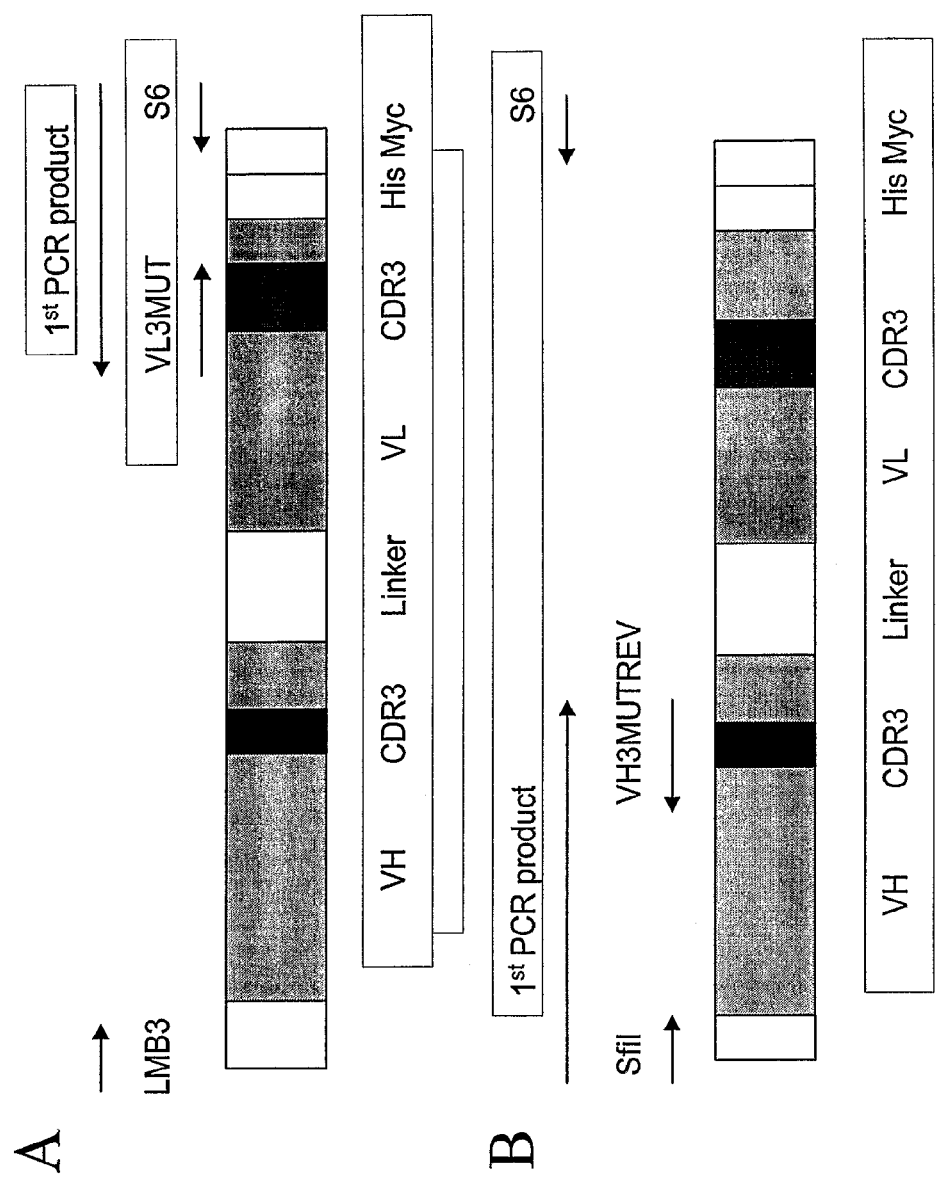
Figure 4. Light chain (A) and Heavy chain (B) CDR3 mutagenesis on pHEN2 G49 vector.

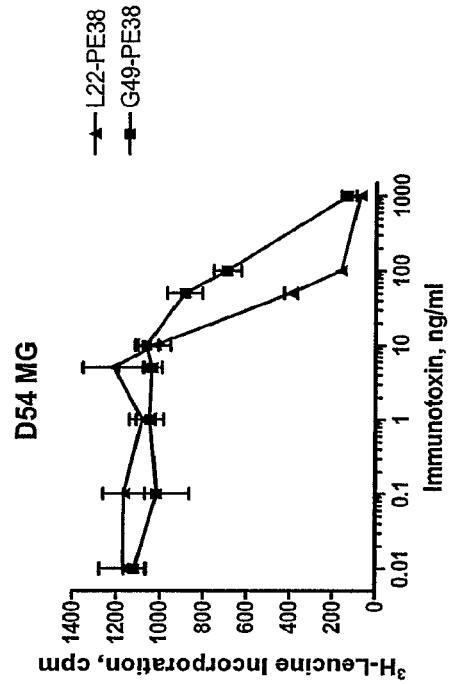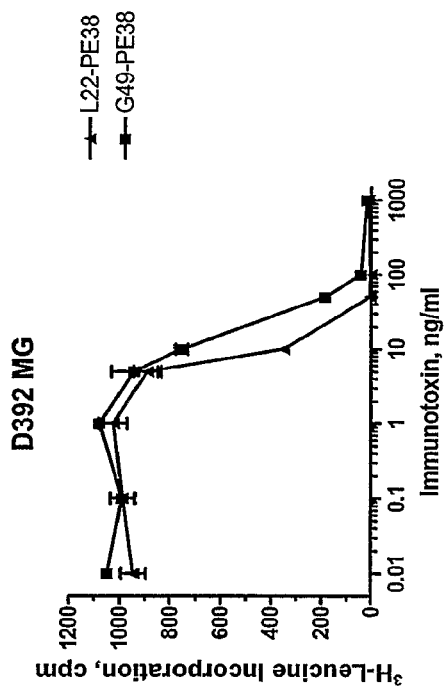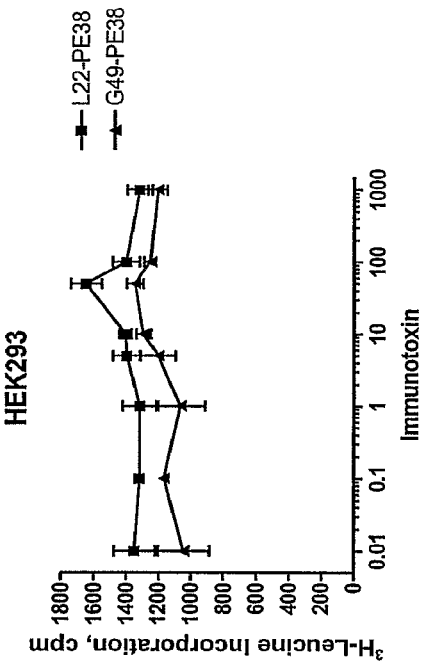
FIGURE 6

Sequence alignment for anti-GPNMB antibody variable heavy chains

HEAVY CHAIN ("V_H")

```
        SEQ ID NO:   ----------FR1----------            -CDR1   -----FR2-------  -CDR2-
G49      1           MAQVQLVQSGAEVKKPGSSVKVSCKASGGTF    SSYAI   SWVRQAPGQGLEWMG  GIIPIF
L22      2           MAQVQLVQSGAEVKKPGSSVKVSCKASGGTF    SSYAI   SWVRQAPGQGLEWMG  GIIPIF
B307     3           MAQVQLVQSGAEVKKPGSSVKVSCKASGGTF    GSYAI   SWVRQAPGQGLEWMG  GIIPIF
902V     4           MAQVQLVQSGAEVKKPGSSVKVSCKASGGTF    GTYAI   SWVRQAPGQGLEWMG  GIIPIF
201      5           MAQVQLVQSGAEVKKPGSSVKVSCKASGGTF    ARTAI   SWVRQAPGQGLEWMG  GIIPIF
B308     6           MAQVQLVQSGAEVKKPGSSVKVSCKASGGTF    SRTAI   SWVRQAPGQGLEWMG  GIIPIF
B305     7           MAQVQLVQSGAEVKKPGSSVKVSCKASGGTF    STTAI   SWVRQAPGQGLEWMG  GIIPIF
L04      8           MAQVQLVQSGAEVKKPGSSVKVSCKASGGTF    SSYAI   SWVRQAPGQGLEWMG  GIIPIF
L12      9           MAQVQLVQSGAEVKKPGSSVKVSCKASGGTF    SSYAI   SWVRQAPGQGLEWMG  GIIPIF
L15     10           MAQVQLVQSGAEVKKPGSSVKVSCKASGGTF    SSYAI   SWVRQAPGQGLEWMG  GIIPIF

G49      GTANYAQKFQG  RVTITADESTSTAYMELSSLRSEDTAVYYCAR  GPNT  WGQGTLVTVSS
L22      GTANYAQKFQG  RVTITADESTSTAYMELSSLRSEDTAVYYCAR  GPNT  WGQGTLVTVSS
B307     GTANYAQKFQG  RVTITADESTSTAYMELSSLRSEDTAVYYCAR  GPNT  WGQGTLVTVSS
902V     GTANYAQKFQG  RVTITADESTSTAYMELSSLRSEDTAVYYCAR  GPNT  WGQGTLVTVSS
201      GTANYAQKFQG  RVTITADESTSTAYMELSSLRSEDTAVYYCAR  GPNT  WGQGTLVTVSS
B308     GTANYAQKFQG  RVTITADESTSTAYMELSSLRSEDTAVYYCAR  GPNT  WGQGTLVTVSS
B305     GTANYAQKFQG  RVTITADESTSTAYMELSSLRSEDTAVYYCAR  GPNT  WGQGTLVTVSS
L04      GTANYAQKFQG  RVTITADESTSTAYMELSSLRSEDTAVYYCAR  GPNT  WGQGTLVTVSS
L12      GTANYAQKFQG  RVTITADESTSTAYMELSSLRSEDTAVYYCAR  GPNT  WGQGTLVTVSS
L15      GTANYAQKFQG  RVTITADESTSTAYMELSSLRSEDTAVYYCAR  GPNT  WGQGTLVTVSS
         ---CRD2----  ---------------FR3-------------  CDR3  ---FR4-----
```

LINKER:   GGGGSGGGGSGGGSA   (SEQ ID NO.:11)

FIGURE 7A

Sequence alignment for anti-GPNMB antibody variable light chains

LIGHT CHAIN ("V_L")

```
       SEQ ID NO:    -------FR1---------        ------CDR1------         ------FR2------
G49       12         LDVVMTQSPLSLPVTPGEPASISC   RSSQSLLHSNGYNYLD         WYLQKPGQSPQLLIY
L22       13         LDVVMTQSPLSLPVTPGEPASISC   RSSQSLLHSNGYNYLD         WYLQKPGQSPQLLIY
B307      14         LDVVMTQSPLSLPVTPGEPASISC   RSSQSLLHSNGYNYLD         WYLQKPGQSPQLLIY
902V      15         LDVVMTQSPLSLPVTPGEPASISC   RSSQSLLHSNGYNYLD         WYLQKPGQSPQLLIY
201       16         LDVVMTQSPLSLPVTPGEPASISC   RSSQSLLHSNGYNYLD         WYLQKPGQSPQLLIY
B308      17         LDVVMTQSPLSLPVTPGEPASISC   RSSQSLLHSNGYNYLD         WYLQKPGQSPQLLIY
B305      18         LDVVMTQSPLSLPVTPGEPASISC   RSSQSLLHSNGYNYLD         WYLQKPGQSPQLLIY
L04       19         LDVVMTQSPLSLPVTPGEPASISC   RSSQSLLHSNGYNYLD         WYLQKPGQSPQLLIY
L12       20         LDVVMTQSPLSLPVTPGEPASISC   RSSQSLLHSNGYNYLD         WYLQKPGQSPQLLIY
L15       21         LDVVMTQSPLSLPVTPGEPASISC   RSSQSLLHSNGYNYLD         WYLQKPGQSPQLLIY

G49       LGSNRAS   GVPDRFSGSGSGTDFTLKISRVEAEDVGVYYC   MQALQTHPT   FGQGTKVEIKR
L22       LGSNRAS   GVPDRFSGSGSGTDFTLKISRVEAEDVGVYYC   METLQTHPT   FGQGTKVEIKR
B307      LGSNRAS   GVPDRFSGSGSGTDFTLKISRVEAEDVGVYYC   METLQTHPT   FGQGTKVEIKR
902V      LGSNRAS   GVPDRFSGSGSGTDFTLKISRVEAEDVGVYYC   METLQTHPT   FGQGTKVEIKR
201       LGSNRAS   GVPDRFSGSGSGTDFTLKISRVEAEDVGVYYC   METLQTHPT   FGQGTKVEIKR
B308      LGSNRAS   GVPDRFSGSGSGTDFTLKISRVEAEDVGVYYC   METLQTHPT   FGQGTKVEIKR
B305      LGSNRAS   GVPDRFSGSGSGTDFTLKISRVEAEDVGVYYC   METLQTHPT   FGQGTKVEIKR
L04       LGSNRAS   GVPDRFSGSGSGTDFTLKISRVEAEDVGVYYC   EPTLQTHPT   FGQGTKVEIKR
L12       LGSNRAS   GVPDRFSGSGSGTDFTLKISRVEAEDVGVYYC   AMTLQTHPT   FGQGTKVEIKR
L15       LGSNRAS   GVPDRFSGSGSGTDFTLKISRVEAEDVGVYYC   GVALQTHPT   FGQGTKVEIKR
          --CDR2-   -------------FR3-------------     ---CDR3--   ----FR4----
```

FIGURE 7B

SEQUENCE LISTING

```
<160> NUMBER OF SEQ ID NOS: 58

<210> SEQ ID NO 1
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody G49 heavy chain varable
      region (V-H)

<400> SEQUENCE: 1

Met Ala Gln Val Gln Leu Val Gln Ser Gly Ala Glu Val Lys Lys Pro
 1               5                  10                  15
```

Gly Ser Ser Val Lys Val Ser Cys Lys Ala Ser Gly Thr Phe Ser
            20                  25                  30

Ser Tyr Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln
 50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
    115

<210> SEQ ID NO 2
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L22 heavy chain varable
      region (V-H)

<400> SEQUENCE: 2

Met Ala Gln Val Gln Leu Val Gln Ser Gly Ala Glu Val Lys Lys Pro
 1               5                  10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln
 50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
    115

<210> SEQ ID NO 3
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B307 heavy chain
      varable region (V-H)

<400> SEQUENCE: 3

Met Ala Gln Val Gln Leu Val Gln Ser Gly Ala Glu Val Lys Lys Pro
 1               5                  10                  15

Gly Ser Ser Val Lys Val Ser Cys Lys Ala Ser Gly Gly Thr Phe Gly
            20                  25                  30

Ser Tyr Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln

```
                    50                  55                  60
Lys Phe Gln Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                    85                  90                  95

Tyr Cys Ala Arg Gly Pro Asn Thr Trp Gly Gln Gly Thr Leu Val Thr
                100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 902V heavy chain
      varable region (V-H)

<400> SEQUENCE: 4

Met Ala Gln Val Gln Leu Val Gln Ser Gly Ala Glu Val Lys Lys Pro
  1               5                  10                  15

Gly Ser Ser Val Lys Val Ser Cys Lys Ala Ser Gly Gly Thr Phe Gly
                 20                  25                  30

Thr Tyr Ala Ile Ser Trp Val Arg Gln Ala Pro Gly Gln Gly Leu Glu
                 35                  40                  45

Trp Met Gly Gly Ile Ile Pro Ile Phe Gly Thr Ala Asn Tyr Ala Gln
                50                  55                  60

Lys Phe Gln Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                    85                  90                  95

Tyr Cys Ala Arg Gly Pro Asn Thr Trp Gly Gln Gly Thr Leu Val Thr
                100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 201 heavy chain varable
      region (V-H)

<400> SEQUENCE: 5

Met Ala Gln Val Gln Leu Val Gln Ser Gly Ala Glu Val Lys Lys Pro
  1               5                  10                  15

Gly Ser Ser Val Lys Val Ser Cys Lys Ala Ser Gly Gly Thr Phe Ala
                 20                  25                  30

Arg Thr Ala Ile Ser Trp Val Arg Gln Ala Pro Gly Gln Gly Leu Glu
                 35                  40                  45

Trp Met Gly Gly Ile Ile Pro Ile Phe Gly Thr Ala Asn Tyr Ala Gln
                 50                  55                  60

Lys Phe Gln Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                    85                  90                  95
```

Tyr Cys Ala Arg Gly Pro Asn Thr Trp Gly Gln Gly Thr Leu Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B308 heavy chain
      varable region (V-H)

<400> SEQUENCE: 6

Met Ala Gln Val Gln Leu Val Gln Ser Gly Ala Glu Val Lys Lys Pro
 1               5                  10                  15

Gly Ser Ser Val Lys Val Ser Cys Lys Ala Ser Gly Gly Thr Phe Ser
            20                  25                  30

Arg Thr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
 50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B305 heavy chain
      varable region (V-H)

<400> SEQUENCE: 7

Met Ala Gln Val Gln Leu Val Gln Ser Gly Ala Glu Val Lys Lys Pro
 1               5                  10                  15

Gly Ser Ser Val Lys Val Ser Cys Lys Ala Ser Gly Gly Thr Phe Ser
            20                  25                  30

Thr Thr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
 50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L04 heavy chain varable
      region (V-H)

<400> SEQUENCE: 8

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L12 heavy chain varable
      region (V-H)

<400> SEQUENCE: 9

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: anti-glycoprotein nonmetastatic melanoma protein B (anti-GPNMB) scFv antibody L15 heavy chain varable region (V-H)

<400> SEQUENCE: 10

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
                20                  25                  30

Ser Tyr Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Asp Thr Ala Val Tyr
                85                  90                  95

Tyr Cys Ala Arg Gly Pro Asn Thr Trp Gly Gln Gly Thr Leu Val Thr
                100                 105                 110

Val Ser Ser
        115

<210> SEQ ID NO 11
<211> LENGTH: 14
<212> TYPE: PRT
<213> ORGANISM: Artificial Sequence
<220> FEATURE:
<223> OTHER INFORMATION: fusion protein spacer or linker

<400> SEQUENCE: 11

Gly Gly Gly Gly Ser Gly Gly Gly Gly Ser Gly Gly Ser Ala
1               5                   10

<210> SEQ ID NO 12
<211> LENGTH: 114
<212> TYPE: PRT
<213> ORGANISM: Artificial Sequence
<220> FEATURE:
<223> OTHER INFORMATION: anti-glycoprotein nonmetastatic melanoma
    protein B (anti-GPNMB) scFv antibody G49 light chain varable
    region (V-L)

<400> SEQUENCE: 12

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr His Pro Thr Phe Gly Gln Gly Thr Lys Val Glu Ile
                100                 105                 110

Lys Arg

<210> SEQ ID NO 13

```
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L22 light chain varable
      region (V-L)

<400> SEQUENCE: 13
```

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg

```
<210> SEQ ID NO 14
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B307 light chain
      varable region (V-L)

<400> SEQUENCE: 14
```

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg

```
<210> SEQ ID NO 15
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 902V light chain
      varable region (V-L)

<400> SEQUENCE: 15
```

```
Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg
```

<210> SEQ ID NO 16
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 201 light chain varable
      region (V-L)

<400> SEQUENCE: 16

```
Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg
```

<210> SEQ ID NO 17
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B308 light chain
      varable region (V-L)

<400> SEQUENCE: 17

```
Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45
```

```
Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg

<210> SEQ ID NO 18
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B305 light chain
      varable region (V-L)

<400> SEQUENCE: 18

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Glu
                85                  90                  95

Thr Leu Gln Thr His Pro Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L04 light chain varable
      region (V-L)

<400> SEQUENCE: 19

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Glu Pro
                85                  90                  95
```

```
Thr Leu Gln Thr His Pro Thr Phe Gly Gln Gly Thr Lys Val Glu Ile
                100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L12 light chain varable
      region (V-L)

<400> SEQUENCE: 20

Leu Asp Val Val Met Thr Gln Ser Pro Leu Ser Leu Pro Val Thr Pro
  1               5                  10                  15

Gly Glu Pro Ala Ser Ile Ser Cys Arg Ser Ser Gln Ser Leu Leu His
               20                  25                  30

Ser Asn Gly Tyr Asn Tyr Leu Asp Trp Tyr Leu Gln Lys Pro Gly Gln
           35                  40                  45

Ser Pro Gln Leu Leu Ile Tyr Leu Gly Ser Asn Arg Ala Ser Gly Val
       50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Ala Met
                 85                  90                  95

Thr Leu Gln Thr His Pro Thr Phe Gly Gln Gly Thr Lys Val Glu Ile
                100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L15 light chain varable
      region (V-L)

<400> SEQUENCE: 21

Leu Asp Val Val Met Thr Gln Ser Pro Leu Ser Leu Pro Val Thr Pro
  1               5                  10                  15

Gly Glu Pro Ala Ser Ile Ser Cys Arg Ser Ser Gln Ser Leu Leu His
               20                  25                  30

Ser Asn Gly Tyr Asn Tyr Leu Asp Trp Tyr Leu Gln Lys Pro Gly Gln
           35                  40                  45

Ser Pro Gln Leu Leu Ile Tyr Leu Gly Ser Asn Arg Ala Ser Gly Val
       50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gly Val
                 85                  90                  95

Ala Leu Gln Thr His Pro Thr Phe Gly Gln Gly Thr Lys Val Glu Ile
                100                 105                 110

Lys Arg

<210> SEQ ID NO 22
<211> LENGTH: 5
```

```
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) antibody G49 heavy chain variable
      region (V-H) complementarity determining region 1 (CDR1)

<400> SEQUENCE: 22

Ser Ser Tyr Ala Ile
1               5

<210> SEQ ID NO 23
<211> LENGTH: 5
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) antibody L22 heavy chain variable
      region (V-H) complementarity determining region 1 (CDR1)

<400> SEQUENCE: 23

Ser Ser Tyr Ala Ile
1               5

<210> SEQ ID NO 24
<211> LENGTH: 5
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B307 heavy chain
      varable region (V-H) complementarity determining region 1 (CDR1)

<400> SEQUENCE: 24

Gly Ser Tyr Ala Ile
1               5

<210> SEQ ID NO 25
<211> LENGTH: 5
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 902V heavy chain
      varable region (V-H) complementarity determining region 1 (CDR1)

<400> SEQUENCE: 25

Gly Thr Tyr Ala Ile
1               5

<210> SEQ ID NO 26
<211> LENGTH: 5
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody 201 heavy chain varable
      region (V-H) complementarity determining region 1 (CDR1)

<400> SEQUENCE: 26

Ala Arg Thr Ala Ile
1               5

<210> SEQ ID NO 27
<211> LENGTH: 5
<212> TYPE: PRT
<213> ORGANISM: Artificial Sequence
<220> FEATURE:
<223> OTHER INFORMATION: anti-glycoprotein nonmetastatic melanoma
``` protein B (anti-GPNMB) scFv antibody B308 heavy chain
varable region (V-H) complementarity determining region 1 (CDR1)

<400> SEQUENCE: 27

Ser Arg Thr Ala Ile
1               5

<210> SEQ ID NO 28
<211> LENGTH: 5
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody B305 heavy chain
      varable region (V-H) complementarity determining region 1 (CDR1)

<400> SEQUENCE: 28

Ser Thr Thr Ala Ile
1               5

<210> SEQ ID NO 29
<211> LENGTH: 17
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody heavy chain varable
      region (V-H) complementarity determining region 2 (CDR2)

<400> SEQUENCE: 29

Gly Ile Ile Pro Ile Phe Gly Thr Ala Asn Tyr Ala Gln Lys Phe Gln
1               5                   10                  15

Gly

<210> SEQ ID NO 30
<211> LENGTH: 4
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody heavy chain varable
      region (V-H) complementarity determining region 3 (CDR3)

<400> SEQUENCE: 30

Gly Pro Asn Thr
1

<210> SEQ ID NO 31
<211> LENGTH: 16
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody light chain varable
      region (V-L) complementarity determining region 1 (CDR1)

<400> SEQUENCE: 31

Arg Ser Ser Gln Ser Leu Leu His Ser Asn Gly Tyr Asn Tyr Leu Asp
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody light chain varable
      region (V-L) complementarity determining region 2 (CDR2)

```
<400> SEQUENCE: 32

Leu Gly Ser Asn Arg Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody G49 light chain varable
      region (V-L) complementarity determining region 3 (CDR3)

<400> SEQUENCE: 33

Met Gln Ala Leu Gln Thr His Pro Thr
1               5

<210> SEQ ID NO 34
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L22, B307, 902V, 201,
      B308 and B305 light chain varable region (V-L) complementarity
      determining region 3 (CDR3)

<400> SEQUENCE: 34

Met Glu Thr Leu Gln Thr His Pro Thr
1               5

<210> SEQ ID NO 35
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L04 light chain varable
      region (V-L) complementarity determining region 3 (CDR3)

<400> SEQUENCE: 35

Glu Pro Thr Leu Gln Thr His Pro Thr
1               5

<210> SEQ ID NO 36
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L12 light chain varable
      region (V-L) complementarity determining region 3 (CDR3)

<400> SEQUENCE: 36

Ala Met Thr Leu Gln Thr His Pro Thr
1               5

<210> SEQ ID NO 37
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L15 light chain varable
      region (V-L) complementarity determining region 3 (CDR3)

<400> SEQUENCE: 37
```

Gly Val Ala Leu Gln Thr His Pro Thr
1               5

<210> SEQ ID NO 38
<211> LENGTH: 729
<212> TYPE: DNA
<213> ORGANISM: Artificial Sequence
<220> FEATURE:
<223> OTHER INFORMATION: anti-glycoprotein nonmetastatic melanoma
      protein B (anti-GPNMB) scFv antibody G49

<400> SEQUENCE: 38

```
atggcccagg tgcagctggt gcagtctggg gctgaggtga agaagcctgg gtcctcggtg      60
aaggtctcct gcaaggcttc tggaggcacc ttcagcagct atgctatcag ctgggtgcga     120
caggcccctg gacaaggtct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcaaga     300
gggcctaata cgtggggcca aggtaccctg gtcaccgtct cgagtggtgg aggcggttca     360
ggcggaggtg gctctggcgg tagtgcactt gatgttgtga tgactcagtc tccactctcc     420
ctgcccgtca cccctggaga gccggcctcc atctcctgca ggtctagtca gagcctcctg     480
catagtaatg gatacaacta tttggattgg tacctgcaga agccagggca gtctccacag     540
ctcctgatct atttgggttc taatcgggcc tccggggtcc ctgacaggtt cagtggcagt     600
ggatcaggca cagattttac actgaaaatc agcagagtgg aggctgagga tgttggggtt     660
tattactgca tgcaagctct acaaactcac cctacgttcg gccaagggac caaggtggaa     720
atcaaacgt                                                            729
```

<210> SEQ ID NO 39
<211> LENGTH: 243
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody G49

<400> SEQUENCE: 39

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Pro Asn Thr Trp Gly Gln Gly Thr Leu Val Thr
            100                 105                 110

Val Ser Ser Gly Gly Gly Gly Ser Gly Gly Gly Gly Ser Gly Gly Ser
        115                 120                 125

Ala Leu Asp Val Val Met Thr Gln Ser Pro Leu Ser Leu Pro Val Thr
    130                 135                 140

Pro Gly Glu Pro Ala Ser Ile Ser Cys Arg Ser Ser Gln Ser Leu Leu

His Ser Asn Gly Tyr Asn Tyr Leu Asp Trp Tyr Leu Gln Lys Pro Gly
            165                 170                 175

Gln Ser Pro Gln Leu Leu Ile Tyr Leu Gly Ser Asn Arg Ala Ser Gly
            180                 185                 190

Val Pro Asp Arg Phe Ser Gly Ser Gly Ser Gly Thr Asp Phe Thr Leu
            195                 200                 205

Lys Ile Ser Arg Val Glu Ala Glu Asp Val Gly Val Tyr Tyr Cys Met
            210                 215                 220

Gln Ala Leu Gln Thr His Pro Thr Phe Gly Gln Gly Thr Lys Val Glu
225                 230                 235                 240

Ile Lys Arg

<210> SEQ ID NO 40
<211> LENGTH: 729
<212> TYPE: DNA
<213> ORGANISM: Artificial Sequence
<220> FEATURE:
<223> OTHER INFORMATION: anti-glycoprotein nonmetastatic melanoma
      protein B (anti-GPNMB) scFv antibody L22

<400> SEQUENCE: 40

```
atggcccagg tgcagctggt gcagtctggg gctgaggtga agaagcctgg gtcctcggtg    60
aaggtctcct gcaaggcttc tggaggcacc ttcagcagct atgctatcag ctgggtgcga   120
caggcccctg gacaaggtct tgagtggatg ggagggatca tccctatctt tggtacagca   180
aactacgcac agaagttcca gggcagagtc acgattaccg cggacgaatc cacgagcaca   240
gcctacatgg agctgagcag cctgagatct gaggacacgg ccgtgtatta ctgtgcaaga   300
gggcctaata cgtggggcca aggtaccctg gtcaccgtct cgagtggtgg aggcggttca   360
ggcggaggtg gctctggcgg tagtgcactt gatgttgtga tgactcagtc tccactctcc   420
ctgcccgtca cccctggaga gccggcctcc atctcctgca ggtctagtca gagcctcctg   480
catagtaatg gatacaacta tttggattgg tacctgcaga agccagggca gtctccacag   540
ctcctgatct atttgggttc taatcgggcc tccggggtcc ctgacaggtt cagtggcagt   600
ggatcaggca cagattttac actgaaaatc agcagagtgg aggctgagga tgttggggtt   660
tattactgca tggagacgct acaaactcac cctacgttcg gccaagggac caaggtggaa   720
atcaaacgt                                                           729
```

<210> SEQ ID NO 41
<211> LENGTH: 243
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L22

<400> SEQUENCE: 41

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
    50                  55                  60

```
Lys Phe Gln Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
             85                  90                  95

Tyr Cys Ala Arg Gly Pro Asn Thr Trp Gly Gln Gly Thr Leu Val Thr
            100                 105                 110

Val Ser Ser Gly Gly Gly Gly Ser Gly Gly Gly Gly Ser Gly Gly Ser
        115                 120                 125

Ala Leu Asp Val Val Met Thr Gln Ser Pro Leu Ser Leu Pro Val Thr
    130                 135                 140

Pro Gly Glu Pro Ala Ser Ile Ser Cys Arg Ser Ser Gln Ser Leu Leu
145                 150                 155                 160

His Ser Asn Gly Tyr Asn Tyr Leu Asp Trp Tyr Leu Gln Lys Pro Gly
                165                 170                 175

Gln Ser Pro Gln Leu Leu Ile Tyr Leu Gly Ser Asn Arg Ala Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Met
    210                 215                 220

Glu Thr Leu Gln Thr His Pro Thr Phe Gly Gln Gly Thr Lys Val Glu
225                 230                 235                 240

Ile Lys Arg

<210> SEQ ID NO 42
<211> LENGTH: 4
<212> TYPE: PRT
<213> ORGANISM: Artificial Sequence
<220> FEATURE:
<223> OTHER INFORMATION: carboxyl terminus sequence for translocation of
      construct into cytosol

<400> SEQUENCE: 42

Lys Asp Glu Leu
 1

<210> SEQ ID NO 43
<211> LENGTH: 4
<212> TYPE: PRT
<213> ORGANISM: Artificial Sequence
<220> FEATURE:
<223> OTHER INFORMATION: carboxyl terminus sequence for translocation of
      construct into cytosol

<400> SEQUENCE: 43

Arg Glu Asp Leu
 1

<210> SEQ ID NO 44
<211> LENGTH: 5
<212> TYPE: PRT
<213> ORGANISM: Artificial Sequence
<220> FEATURE:
<223> OTHER INFORMATION: native Pseudomonas exotoxin carboxyl terminus
      sequence

<400> SEQUENCE: 44

Arg Glu Asp Leu Lys
 1               5

<210> SEQ ID NO 45
```

```
<211> LENGTH: 5
<212> TYPE: PRT
<213> ORGANISM: Artificial Sequence
<220> FEATURE:
<223> OTHER INFORMATION: linker repeat motif

<400> SEQUENCE: 45

Gly Gly Gly Gly Ser
 1               5

<210> SEQ ID NO 46
<211> LENGTH: 27
<212> TYPE: DNA
<213> ORGANISM: Artificial Sequence
<220> FEATURE:
<223> OTHER INFORMATION: anti-glycoprotein nonmetastatic melanoma
      protein B (anti-GPNMB) scFv antibody G49 light chain varable
      region (V-L) complementarity determining region 3 (CDR3)

<400> SEQUENCE: 46
atgcaagctc tacaaactca ccctacg                                      27

<210> SEQ ID NO 47
<211> LENGTH: 12
<212> TYPE: DNA
<213> ORGANISM: Artificial Sequence
<220> FEATURE:
<223> OTHER INFORMATION: anti-glycoprotein nonmetastatic melanoma
      protein B (anti-GPNMB) scFv antibody G49 heavy chain varable
      region (V-H) complementarity determining region 3 (CDR3)

<400> SEQUENCE: 47
gggcctaata cg                                                      12

<210> SEQ ID NO 48
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody light chain varable
      region (V-L) complementarity determining region 3 (CDR3) L1
      library
<221> NAME/KEY: MOD_RES
<222> LOCATION: (1)...(3)
<223> OTHER INFORMATION: Xaa = any amino acid

<400> SEQUENCE: 48

Xaa Xaa Xaa Leu Gln Thr His Pro Thr
 1               5

<210> SEQ ID NO 49
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody light chain varable
      region (V-L) complementarity determining region 3 (CDR3) L2
      library
<221> NAME/KEY: MOD_RES
<222> LOCATION: (4)...(6)
<223> OTHER INFORMATION: Xaa = any amino acid

<400> SEQUENCE: 49

Met Gln Ala Xaa Xaa Xaa His Pro Thr
 1               5

<210> SEQ ID NO 50
```

```
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody light chain varable
      region (V-L) complementarity determining region 3 (CDR3) L3
      library
<221> NAME/KEY: MOD_RES
<222> LOCATION: (7)...(9)
<223> OTHER INFORMATION: Xaa = any amino acid

<400> SEQUENCE: 50

Met Gln Ala Leu Gln Thr Xaa Xaa Xaa
1               5

<210> SEQ ID NO 51
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L21 light chain varable
      region (V-L) complementarity determining region 3 (CDR3)

<400> SEQUENCE: 51

Leu Pro Thr Leu Gln Thr His Pro Thr
1               5

<210> SEQ ID NO 52
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L16 light chain varable
      region (V-L) complementarity determining region 3 (CDR3)

<400> SEQUENCE: 52

Gly Pro Thr Leu Gln Thr His Pro Thr
1               5

<210> SEQ ID NO 53
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L08 light chain varable
      region (V-L) complementarity determining region 3 (CDR3)

<400> SEQUENCE: 53

Ala Val Ala Leu Gln Thr His Pro Thr
1               5

<210> SEQ ID NO 54
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L24 light chain varable
      region (V-L) complementarity determining region 3 (CDR3)

<400> SEQUENCE: 54

Gly Leu Ala Leu Gln Thr His Pro Thr
1               5

<210> SEQ ID NO 55
```

```
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L20 light chain varable
      region (V-L) complementarity determining region 3 (CDR3)

<400> SEQUENCE: 55

Gly Leu Thr Leu Gln Thr His Pro Thr
1               5

<210> SEQ ID NO 56
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L18 light chain varable
      region (V-L) complementarity determining region 3 (CDR3)

<400> SEQUENCE: 56

Val Met Thr Leu Gln Thr His Pro Thr
1               5

<210> SEQ ID NO 57
<211> LENGTH: 8
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L07 light chain varable
      region (V-L) complementarity determining region 3 (CDR3)

<400> SEQUENCE: 57

His Met Ser Leu Gln Thr His Pro
1               5

<210> SEQ ID NO 58
<211> LENGTH: 9
<212> TYPE: PRT
<213> ORGANISM: Artificial Sequence
<220> FEATURE:
<223> OTHER INFORMATION: anti-glycoprotein nonmetastatic melanoma
      protein B (anti-GPNMB) scFv antibody L11 light chain varable
      region (V-L) complementarity determining region 3 (CDR3)

<400> SEQUENCE: 58

Glu Arg Trp Leu Gln Thr His Pro Thr
1               5
```

ANTIBODIES AND IMMUNOTOXINS THAT TARGET HUMAN GLYCOPROTEIN NMB

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Targeting of cell surface proteins on cancer cells is a modern approach for cancer therapy. Targeted cytotoxins are 5-10 times more potent on cancer cells than chemotherapy and provide specificity without producing undesirable side effects (Frankel, A. E. et al., *Cancer Res.* 56, 926-932 (1996); Rand, R. W. et al., *Clin. Cancer Res.* 6, 2157-2165 (2000)). To generate a targeted agent, identification of unique cancer cell-associated receptors or antigens is important.

Recent advances in the development of comprehensive molecular analysis tools for genome and gene expression provide a basis to discover novel target molecules with tumor-specific distribution (Velculescu et al., *Science,* 270:484-7 (1995)). In previous efforts to identify novel glioma-associated antigens, several genes were found by the serial analysis of gene expression method that are preferentially expressed in gliomas (Loging et al., *Genome Res,* 10:1393-402 (2000)). Among these candidate glioma-marker genes, glycoprotein nmb (GPNMB) showed a greater than 10-fold induction of mRNA expression over normal brain samples in 5/12 of HGL cases (Loging et al., supra).

Glycoprotein nonmetastatic melanoma protein B ("GPNMB") is a type I transmembrane protein which was isolated from a subtractive cDNA library based on differential expression between human melanoma cell lines with low and high metastatic potential in nude mice. gpnmb mRNA was also expressed at high levels in low-metastatic melanoma cell lines and xenografts (Weterman et al., *Int J Cancer,* 60:73-81 (1995)). Human GPNMB exists both in its native form ("GPNMBwt") and a splice variant form in which there is a 12-amino acid in-frame insertion in the extracellular domain ("GPNMBsv")

Immunotoxins have been made that recognize a wide variety of cell-surface targets on cancer cells. Typically these are tumor-associated antigens—i.e., antigens that are overexpressed on cancer cells relative to normal cells. It would be desirable to have immunotoxins useful for inhibiting the growth of cells expressing GPNMB.

BRIEF SUMMARY OF THE INVENTION

The invention provides antibodies against human glycoprotein NMB and methods for using them. In a first group of embodiments, the invention provides isolated polypeptides comprising an antibody heavy chain variable region ("VH") and an antibody light chain variable region ("VL"), each variable region having an amino terminus and a carboxyl terminus and comprising four framework regions ("FRs"), which FRs are numbered sequentially FRs 1-4 starting from the amino terminus, and three complementarity determining regions ("CDRs"), which CDRs of each region are numbered sequentially CDR1 to CDR3 starting from the amino terminus, wherein CDR1 of said VH has a sequence selected from the group consisting of SEQ ID NOs:22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37. In some embodiments, the CDR1 of said VH chain of said polypeptide has the sequence of SEQ ID NO:23 and said CDR3 of said VL chain has the sequence of SEQ ID NO:34. In some embodiments, the CDR1 of said VH chain of said polypeptide has the sequence of SEQ ID NO:24 and said CDR3 of said VL chain has the sequence of SEQ ID NO:34. In some embodiments, the CDR1 of said VH chain of said polypeptide has the sequence of SEQ ID NO:25 and said CDR3 of said VL chain has the sequence of SEQ ID NO:34. In some embodiments, the CDR1 of said VH chain of said polypeptide has the sequence of SEQ ID NO:26 and said CDR3 of said VL chain has the sequence of SEQ ID NO:34. In some embodiments, the FRs 1-4, respectively, of said VH have the sequence of FRs 1-4, respectively, of the VH of antibody G49 as shown in FIG. 7 and wherein FRs 1-4, respectively, of said VL have the sequence of FRs 1-4, respectively, of the VL of antibody G49 as shown in FIG. 7.

In a further group of embodiments, the invention provides chimeric molecules, comprising (a) a polypeptide comprising an antibody heavy chain variable region ("VH") and an antibody light chain variable region ("VL"), each variable region having an amino terminus and a carboxyl terminus and comprising four framework regions ("FRs"), which FRs are numbered sequentially FRs 1-4 starting from the amino terminus, and three complementarity determining regions ("CDRs"), which CDRs of each region are numbered sequentially CDR1 to CDR3 starting from the amino terminus, wherein CDR1 of said VH has a sequence selected from the group consisting of SEQ ID NOs:22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37, and (b) an effector molecule selected from the group consisting of a detectable label, a radionuclide, and a therapeutic agent. In some embodiments, the CDR1 of said VH chain of said polypeptide has the sequence of SEQ ID NO:23 and said CDR3 of said VL chain has the sequence of SEQ ID NO:34. In some embodiments, the CDR1 of said VH chain of said polypeptide has the sequence of SEQ ID NO:24 and said CDR3 of said VL chain has the sequence of SEQ ID NO:34. In some embodiments, the CDR1 of said VH chain of said polypeptide has the sequence of SEQ ID NO:25 and said CDR3 of said VL chain has the sequence of SEQ ID NO:34. In some embodiments, the CDR1 of said VH chain of said polypeptide has the sequence of SEQ ID NO:26 and said CDR3 of said VL chain has the sequence of SEQ ID NO:34. In some embodiments, the FRs 1-4, respectively, of said VH have the sequence of FRs 1-4, respectively, of the VH of antibody G49 as shown in FIG. 7 and wherein FRs 1-4, respectively, of said VL have the sequence of FRs 1-4, respectively, of the VL of antibody G49 as shown in FIG. 7. In some embodiments, the effector molecule is a therapeutic agent. In some embodiments, the therapeutic agent is a cytotoxin. In some embodiments, the cytotoxin is a *Pseudomonas* exotoxin A (PE). In some embodiments, the PE is selected from the group consisting of PE4E, PE35, PE37, PE38, PE38QQR, PE38 KDEL, and PE40.

In yet another group of embodiments, the invention provides compositions comprising any of the chimeric molecules described in the preceding paragraph, and a pharmaceutically acceptable carrier.

In still another group of embodiments, the invention provides isolated nucleic acids encoding a polypeptide comprising an antibody heavy chain variable region ("VH") and an antibody light chain variable region ("VL"), each variable region having an amino terminus and a carboxyl terminus and comprising four framework regions ("FRs"), which FRs are numbered sequentially FRs 1-4 starting from the amino terminus, and three complementarity determining regions ("CDRs"), which CDRs of each region are numbered sequentially CDR1 to CDR3 starting from the amino terminus, wherein CDR1 of said VH has a sequence selected from the group consisting of SEQ ID NOs:22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37. In some embodiments, the CDR1 of said VH chain of said polypeptide has the sequence of SEQ ID NO:23 and said CDR3 of said VL chain has the sequence of SEQ ID NO:34. In some embodiments, the CDR1 of said VH chain of said polypeptide has the sequence of SEQ ID NO:24 and said CDR3 of said VL chain has the sequence of SEQ ID NO:34. In some embodiments, the CDR1 of said VH chain of said polypeptide has the sequence of SEQ ID NO:25 and said CDR3 of said VL chain has the sequence of SEQ ID NO:34. In some embodiments, the CDR1 of said VH chain of said polypeptide has the sequence of SEQ ID NO:26 and said CDR3 of said VL chain has the sequence of SEQ ID NO:34. In some embodiments, the FRs 1-4, respectively, of said VH have the sequence of FRs 1-4, respectively, of the VH of antibody G49 as shown in FIG. 7 and wherein FRs 1-4, respectively, of said VL have the sequence of FRs 1-4, respectively, of the VL of antibody G49 as shown in FIG. 7. In some embodiments, the nucleic acid further encodes an effector moiety fused to the polypeptide. In some embodiments, the effector moiety is a cytotoxin. In some embodiments, the cytotoxin is a *Pseudomonas* exotoxin A ("PE"). In some embodiments, the PE is selected from the group consisting of PE4E, PE35, PE37, PE38, PE38QQR, PE38 KDEL, and PE40.

In a further group of embodiments, the invention provides methods of inhibiting the growth of a cancer cell expressing human glycoprotein NMB, said method comprising contacting said cell with a chimeric molecule comprising (a) a polypeptide comprising an antibody heavy chain variable region ("VH") and an antibody light chain variable region ("VL"), each variable region having an amino terminus and a carboxyl terminus and comprising four framework regions ("FRs"), which FRs are numbered sequentially FRs 1-4 starting from the amino terminus, and three complementarity determining regions ("CDRs"), which CDRs of each region are numbered sequentially CDR1 to CDR3 starting from the amino terminus, wherein CDR1 of said VH has a sequence selected from the group consisting of SEQ ID NOs:22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37, and (b) a therapeutic agent, wherein contacting said cell with said agent inhibits the growth of said cell. In some embodiments, the CDR1 of said VH chain of said polypeptide has the sequence of SEQ ID NO:23 and said CDR3 of said VL chain has the sequence of SEQ ID NO:34. In some embodiments, the CDR1 of said VH chain of said polypeptide has the sequence of SEQ ID NO:24 and said CDR3 of said VL chain has the sequence of SEQ ID NO:34. In some embodiments, the CDR1 of said VH chain of said polypeptide has the sequence of SEQ ID NO:25 and said CDR3 of said VL chain has the sequence of SEQ ID NO:34. In some embodiments, the CDR1 of said VH chain of said polypeptide has the sequence of SEQ ID NO:26 and said CDR3 of said VL chain has the sequence of SEQ ID NO:34. In some embodiments, the FRs 1-4, respectively, of said VH have the sequence of FRs 1-4, respectively, of the VH of antibody G49 as shown in FIG. 7 and wherein FRs 1-4, respectively, of said VL have the sequence of FRs 1-4, respectively, of the VL of antibody G49 as shown in FIG. 7. In some embodiments, the therapeutic agent is a cytotoxin. In some embodiments, the cytotoxin is a *Pseudomonas* exotoxin A (PE). In some embodiments, the cancer cell is selected from the group consisting of a glioblastoma multiforme cell, an anaplastic astrocytoma cell, an anaplastic oligodendroglioma, an oligodendroglioma cell, and a melanoma cell.

In a further group of embodiments, the invention provides methods of detecting the presence of a cancer cell expressing human glycoprotein NMB, said method comprising contacting said cell with a chimeric molecule comprising (a) a polypeptide comprising an antibody heavy chain variable region ("VH") and an antibody light chain variable region ("VL"), each variable region having an amino terminus and a carboxyl terminus and comprising four framework regions ("FRs"), which FRs are numbered sequentially FRs 1-4 starting from the amino terminus, and three complementarity determining regions ("CDRs"), which CDRs of each region are numbered sequentially CDR1 to CDR3 starting from the amino terminus, wherein CDR1 of said VH has a sequence selected from the group consisting of SEQ ID NOs:22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37, and (b) a detectable label, and detecting the presence of the label bound to said cell, thereby detecting the presence of said cell. In some embodiments, the CDR1 of said VH chain of said polypeptide has the sequence of SEQ ID NO:23 and said CDR3 of said VL chain has the sequence of SEQ ID NO:34. In some embodiments, the CDR1 of said VH chain of said polypeptide has the sequence of SEQ ID NO:24 and said CDR3 of said VL chain has the sequence of SEQ ID NO:34. In some embodiments, the CDR1 of said VH chain of said polypeptide has the sequence of SEQ ID NO:25 and said CDR3 of said VL chain has the sequence of SEQ ID NO:34. In some embodiments, the CDR1 of said VH chain of said polypeptide has the sequence of SEQ ID NO:26 and said CDR3 of said VL chain has the sequence of SEQ ID NO:34. In some embodiments, the FRs 1-4, respectively, of said VH have the sequence of FRs 1-4, respectively, of the VH of antibody G49 as shown in FIG. 7 and wherein FRs 1-4, respectively, of said VL have the sequence of FRs 1-4, respectively, of the VL of antibody G49 as shown in FIG. 7.

Bis-Tris gel under non-reducing conditions. Positions of size markers in kD are indicated on the left.

Figure 2:
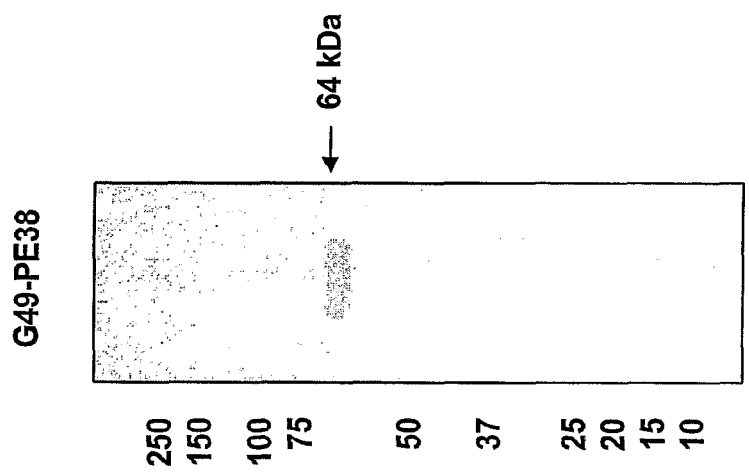

FIG. 2 is a photograph of an SDS-PAGE gel of electrophoresed G49-PE38 immunotoxin. Two µg of G49-PE38 (64 kD, indicated by an arrow) was electrophoresed under non-reducing conditions. Positions of size markers in kD are indicated on the left.

Figure 3A:
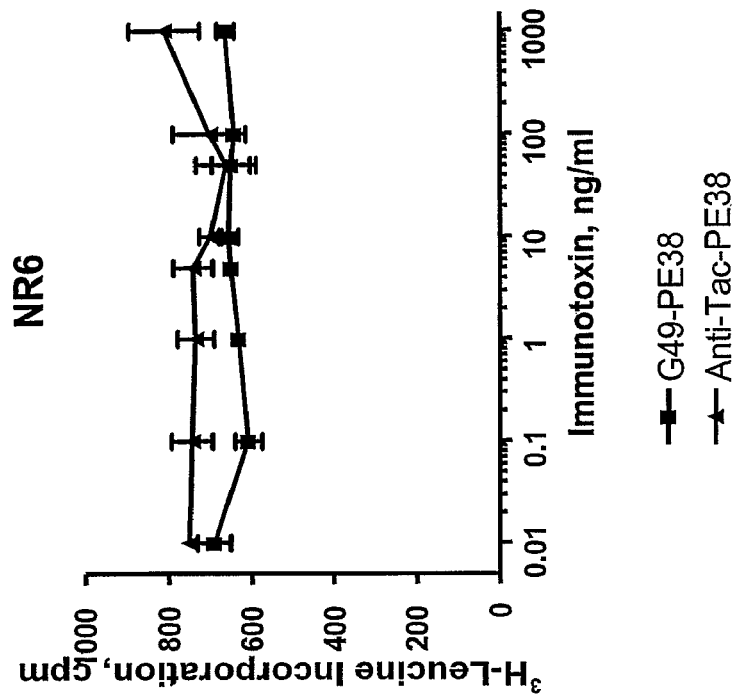
Figure 3B:
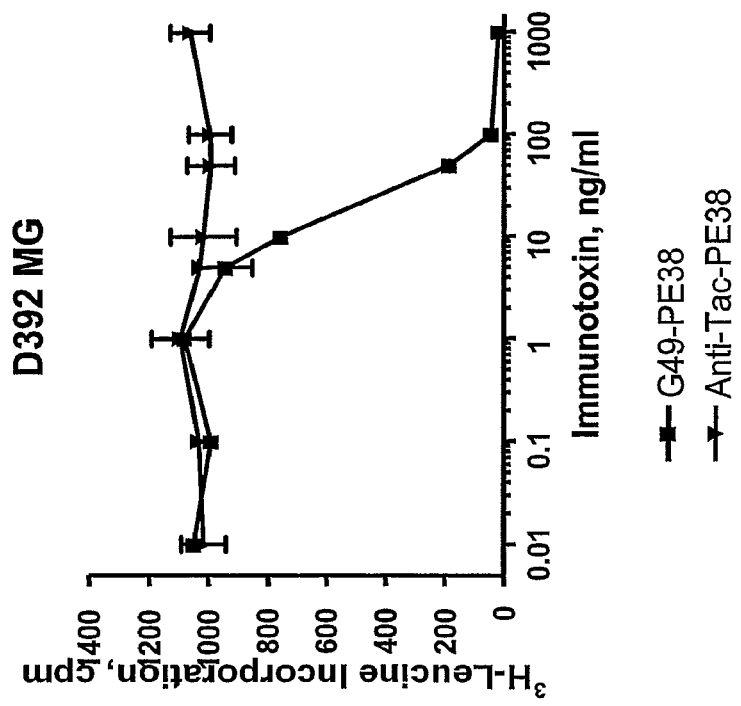

FIG. 3A shows the results of cytotoxicity assays of two immunotoxins, G49-PE38 and anti-TAC-PE38 (which binds to the IL-2 receptor a chain and was used as a control in this study), on a GPNMB-expressing glioma cell line, D392 MG. FIG. 3B shows the results of cytotoxicity assays of the same two immunotoxins on a fibroblast cell line, NR6, that does not express GPNMB. Both Figures: Squares: G49-PE38 immunotoxin. Triangles: Anti-Tac-PE38. Vertical axis: incorporation of $^3$H-Leucine, in cpm. Horizontal axis: Concentration of immunotoxin, in ng/ml.

FIGS. 4A and 4B are cartoons showing the construction of phagemid vectors for mutation of the $V_H$ CDR3 (FIG. 4A) and $V_L$ CDR3s (FIG. 4B) of G49 using degenerate oligonucleotide PCR primers each randomizing three consecutive amino acids.

Figure 5:
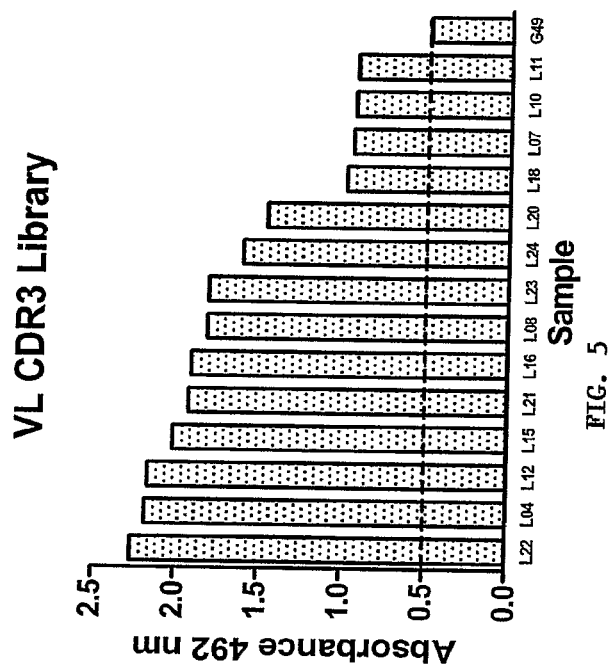

FIG. 5 shows the results of ELISA studies showing that the 14 mutant phage clone samples identified with designators starting with the letter "L" on the horizontal axis had an ELISA signal stronger than that of the parental clone, G49. The absorbance at 492 nm is shown on the vertical axis.

FIGS. 6A-C are graphs showing the cytotoxicity of immunotoxins L22-PE38 and G49-PE38 on GPNMB+ and on GPNMB– cells. FIG. 6A: cytotoxicity of the immunotoxins to GPNMB+ cell line D392 MG. FIG. 6B: cytotoxicity of the immunotoxins to GPNMB– cell line HEK293. FIG. 6C: cytotoxicity of the immunotoxins to GPNMB+ cell line D54MG. All Figures: Squares: G49-PE38 immunotoxin. Triangles: L22-PE38 immunotoxin. Vertical axes: incorporation of $^3$H-Leucine, in cpm. Horizontal axes: Concentration of immunotoxin, in ng/ml.

FIG. 7A is an alignment of the amino acid sequences of the heavy chains of antibodies G49, L22, B307, 902V, 201, B308, B305, L04, L12, and L15 (SEQ ID NOS:1-10), and the sequence of a linker (SEQ ID NO:11) connecting the heavy chain to the light chain in the scFvs of these antibodies. FIG. 7B is an alignment of the amino acid sequences of the light chains of antibodies G49, L22, B307, 902V, 201, B308, B305, L04, L12, and L15 (SEQ ID NOS:12-21). The framework regions ("FRs") and complementarity determining regions ("CDRs") for each chain are labeled; the sequences of the CDRs are shown in bold face. In FIG. 7A, the residues of the scFv G49 heavy chain CDR1 that were mutated to form scFvs B307, 902V, 201, B308, and B305 are underlined. In FIG. 7B, the residues of the VL CDR3 of G49 that were mutated to form scFvs L22, B307, 902V, 201, B308, B305, L04, L12, and L15 are underlined.

DETAILED DESCRIPTION

Introduction

The human transmembrane glycoprotein nonmetastatic melanoma protein B ("GPNMB") and a splice variant form in which there is an in-frame insertion of 12 amino acids in the extracellular domain of the protein have been found to be highly expressed in the cells several forms of brain cancer, as compared to normal brain cells. In particular, both the protein and its splice variant have been found to be overexpressed in glioblastoma multiformes, anaplastic astrocytomas, anaplastic oligodendrogliomas, and oligodendroglioma. See, Kuan et al., Proc Amer Assoc Cancer Research 43:277 (2002). GPNMB is also expressed on some melanoma cells. Accordingly, it would be useful to be able to target agents preferentially to cells expressing GPNMB or its splice variant.

The present invention provides new antibodies that bind GPNMB and to its splice variant with high affinity. It will be appreciated that intact antibodies are bivalent, while scFv and dsFv are monovalent, and that creating scFv or dsFv from an intact antibody typically results in a consequent loss of affinity compared to the antibody used as a starting material. Accordingly, to promote binding of immunoconjugates, such as immunotoxins, to the target cells, it is desirable that the antibody from which the scFv or dsFv is generated has a high affinity for the target antigen. Thus, the antibodies are useful agents for targeting labels, as well as toxins and other therapeutic agents, to GPNMB-expressing cells.

Two of the present inventors previously reported that they were able to generate monoclonal antibodies against GPNMB. Kuan et al., Proc Amer Acad Cancer Res 44:1116-7 (2003). It turned out, however, that these antibodies did not internalize well. This made the antibodies unsuitable for use as the targeting portion of immunotoxins since they would not facilitate internalization of the cytotoxin portion of the immunotoxin into the target cell. As is appreciated by those of skill in the art, cytotoxins must be internalized into a cell to kill it. Unfortunately, the reasons one antibody is internalized and another is not are not well understood, and it is not possible to predict which antibodies will internalize and which will not. Further, although improving the affinity of the targeting portion of the immunotoxin tends to increase the time the immunotoxin binds to the cell and therefore improves its opportunity to be internalized, affinity of the targeting portion of the immunotoxin, by itself, does not necessarily correlate with the immunotoxins' cell-killing ability. For example, the immunotoxin may not be trafficked within the cell in a manner permitting release of the toxin portion into the cytosol. The antibodies that were generated by traditional immunization formats proved unsuitable for targeting cytotoxins to GPNMB-expressing cells.

In light of the failure to obtain antibodies that internalized through monoclonal antibody approaches, another approach was undertaken. This resulted in the discovery of the scFv designated as "G49", and a variant designated as "L22". Further work resulted in the discovery of additional variants of G49 or of L22, designated "B307", "902V," "201", "B308", "B305," "L04", "L12", and "L15", respectively (the sequences of each of these antibodies is discussed in detail below). Surprisingly, and unlike the antibodies generated by immunizing animals, these antibodies not only have high affinity for GPNMB, but also internalize well. Further, when expressed as a recombinant immunotoxin, G49 had significant cytotoxic effect on GPNMB-expressing cells, while the others showed surprisingly higher cytotoxicity to GPNMB-expressing cells than did a like G49-based immunotoxin (except for L15, which had the same cytotoxicity as did G49). Thus, the anti-GPNMB antibodies of the invention are surprisingly useful agents for targeting cytotoxins to GPNMB-expressing cells.

It should be noted that, even though the antibodies of the invention internalize well, they are still expected to remain on the surface of target cells long enough before internalization so that they are still useful agents for delivery of detectable labels for detection of GPNMB-expressing cells in a biological sample or for imaging the location of GPNMB-expressing cells in a patient. Thus, while the monoclonal antibodies previously available could be used for labeling GPNMB-expressing cells, or for carrying to target cells radionuclides or other agents that do not need to enter cells to be effective, they are not useful for making immunotoxins. In contrast, the antibodies of the invention can be used for labeling GPNMB-expressing cells, for delivering to them agents that do not have to enter the cell to be effective, and can be used to make immunotoxins. The antibodies of the invention therefore have a broader range of uses than the anti-GPNMB antibodies previously reported in the art, and have uses for which the antibodies previously available in the art are unsuitable.

Immunotoxins are typically produced by expressing the recombinant immunotoxins in *E. coli*, where they accumulate in inclusion bodies. After the inclusion bodies are washed extensively, they are dissolved in guanidine hydrochloride and the protein renatured and purified by ion-exchange chromatography and gel filtration. To ease processing and cost concerns, it is advantageous if the immunotoxin can be produced with a high yield. Often, however, immunotoxins can only be produced with a yield of a few percent.

In one group of embodiments, therefore, the invention provides the anti-GPNMB antibodies designated by the inventors as G49, L22, B307, 902V, 201, B308, B305, L04, L12, and L15. The Fv regions of these antibodies are shown in FIGS. 7A and B, which set forth the sequences of the variable heavy chain of each of these antibodies, the sequence of an exemplar peptide (SEQ ID NO:11) used in the studies reported in the Examples to link the antibody heavy and light chains, and the sequences of the variable light chains of the antibodies. (For clarity, it is noted that the entire sequence of the variable heavy or light chain for each antibody could not be set forth on a single line in FIGS. 7A and 7B. The SEQ ID NO: shown on the first line for the heavy and for the light chain of each antibody therefore relate to the sequence of the entire chain, not just the sequence shown on the first line. Thus, there is no separate sequence number shown for the second line since the second line is a continuation of the sequence already identified by the SEQ ID NO: for the heavy or light chain in question.) The four framework regions ("FRs") of each chain of each antibody are labeled and numbered, as are the complementarity determining regions ("CDRs") 1, 2 and 3 of each chain. The residues at which the antibodies diverge from those of G49 are underlined. As can be seen, in CDR1 of the VH chain, G49, L22, L04, L12, and L15 have the same sequence, while B307 has a single substitution (of glycine for the first serine), 902V has two and, 201, B308, and B305 all have three. In CDR3 of the VL chain, six of the nine variants of G49 have a glutamic acid and a threonine at positions two and three, respectively, of the CDR, while two variants mutate all three of the first three positions of the CDR and one variant of G49 (L15) contains mutations of just the first two positions of the CDR.

As set forth in the Examples, the inventors discovered the G49 antibody, which has an affinity ($K_D$) for the extracellular domain of GPNMB of 9.1 nM. When made into an immunotoxin using a potent cytotoxin, a 38 kD truncated form of *Pseudomonas* exotoxin A known as "PE38," the resulting immunotoxin inhibited protein synthesis by 50% at a concentration of 30 ng/ml in an exemplar GPNMB-expressing cell line (cell line D392MG) when the cells were exposed to the immunotoxin for 24 hours. In contrast, at concentrations of over 1000 ng/ml, the immunotoxin did not inhibit protein synthesis by 50% in a control cell line, HEK293, that does not express GPNMB. (The amount of an agent which inhibits protein synthesis by 50% is known as the "$IC_{50}$" of the agent, and is considered an important measure of the cytotoxicity of the agent.) See, Table 5, below.

As further shown in the Examples, mutating two residues in the $V_L$ CDR3 that are encoded by codons with nucleotides which fall within a so-called "hot spot motif" Pu-G-Py-ALT (wherein "Pu" refers to a purine base and "Py" refers to a pyrimidine base) resulted in dramatically increasing the cytotoxicity when the resulting antibody, designated L22, was used in place of the G49 antibody in an exemplar immunotoxin. As shown in Table 5 and FIG. 6, using the same linker peptide and the same toxic moiety to permit ready comparison, the cytotoxicity of the L22-PE38 construct was tested against that of G49-PE38. Remarkably, despite only a two amino acid difference between the two constructs, the L22-PE38 construct was 5 times as cytotoxic as G49-PE38 on one GPNMB-expressing cell line (cell line D392MG), and more than 3 times as cytotoxicity as G49-PE38 on another (D54MG). Further, when "hot spot" mutations were made in the VH CDR1, mutating a single residue of L22 (resulting in the B307 antibody) was found to increase cytotoxicity of the immunotoxin another 3 times against the D392MG cell line and 5 times against the D54MG cell line, with no apparent increase in cytotoxicity against the control cell line. Moreover, mutation of a second residue of the VH CDR1, resulting in the 902V antibody, resulted in yet a further doubling of cytotoxicity against the D392MG cell line of an immunotoxin made with the resulting antibody, and a further tripling of cytotoxicity against the D54MG cell line. As shown by Table 5, the immunotoxin made with the 902V antibody was 30 times more cytotoxic to the D392MG cell line than was a like immunotoxin made with G49 as the targeting portion, and was 50 times more cytotoxic to the D54MG cell line than was the like immunotoxin made with G49 as the targeting portion.

The sequences of the VH CDR 1 for the antibodies are SEQ ID NOs:22-28, respectively. As shown in FIG. 7, all the antibodies share the same sequence for VH CDR2 (SEQ ID NO:29) and for VH CDR3 (SEQ ID NO:30). As shown in FIG. 7, all the antibodies also share the same sequences for VL CDR1 (SEQ ID NO:31) and for VL CDR2 (SEQ ID NO:32), but show a variation in the first three residues of the VL CDR3 of G49 (SEQ ID NO:33).

Persons of skill in the art will recognize that it is the complementarity determining regions ("CDRs") that are responsible for an antibody's specificity and affinity, while the framework regions contribute more generally to the 3-dimensional shape and configuration of the molecule and have less impact on the antibody's specificity and affinity. Persons of skill are also aware that, for example, conservative substitutions can typically be made in the framework regions (four of which are present in each variable light and heavy chain), without significantly affecting antigen binding or specificity. The sequences of each of the FR regions of the VH and of the VL chains of the antibodies are shown in FIG. 7.

Persons of skill will also appreciate that the Fv region of the antibody is the portion that binds antigen, while the Fc region of the antibody is involved in opsonization or other effector functions. Further, persons of skill will appreciate that the Fc region is relatively invariant for any given class of immunoglobulin (that is, IgG, IgM, IgA, etc.). Thus, any given Fv region could be grafted onto a Fc section to form an intact immunoglobulin if desired. Since smaller molecules tend to have better tumor penetration than do larger molecules, however, it is usually desirable to use antibody fragments that retain antigen recognition rather intact immunoglobulin, as the targeting portion of immunotoxins intended for use against solid tumors. Thus, the variable light and the variable heavy chains that constitute a Fv region are typically linked, either through a linker, to form a construct known as a scFv, or by engineering cysteines into the framework region to permit formation of a disulfide bond between the chains, thereby creating a construct known as a dsFv.

It will be appreciated that changes can be made in the antibodies described herein, such as changes in the framework regions, without significantly affecting the ability of the antibody to bind GPNMB. Thus, an antibody can readily be engineered which has the CDRs of the antibodies as shown in FIG. 7, but which does not have framework regions ("FRs") having the sequence of those of these antibodies as described herein (since all the antibodies share the FRs of the G49 antibody, for convenience, the FRs are sometimes referred to herein as the FRs of the G49 antibody). To take some simple examples, a practitioner could make a conservative substitution of one residue in one FR in one chain of the Fv, or of one residue in each FR of one chain, or in each FR in each chain. For example, the practitioner could substitute a lysine ("K") for the arginine ("R") which is the last residue shown for the VL FR4 in FIG. 4 to preserve the positive charge the arginine would be expected to have at physiological pH. Similarly, an aspartic acid ("D") could be substituted for the glutamic acid ("E") found at the 12th position in the VH FR1 to provide a substitution preserving the negative charge that the glutamic acid residue would be expected to have at physiological pH. The resulting antibodies could then be readily tested to confirm that the mutations did not affect the binding, cytotoxicity or yield of immunotoxins made with the mutated antibody. Thus, the anti-GPNMB antibodies of the invention encompass antibodies that bind GPNMB and that comprise the VH CDR and the VL CDR sequences of the antibodies described herein, whether or not the sequence of the FRs is fully that of the G49 antibody.

The framework regions (non-CDR regions) of antibodies derived from non-human species can be engineered to replace residues found at particular positions in the antibodies the of non-human animals, such as mice, with residues more typically found at the same position in human antibodies. Antibodies engineered in these ways are referred to as "humanized antibodies" and are preferred, since they have a lower risk of inducing side effects and typically can remain in the circulation longer. Methods of humanizing antibodies are, however, known in the art and are set forth in, for example, U.S. Pat. Nos. 6,180,377; 6,407,213; 5,693,762; 5,585,089; and 5,530,101. The antibodies described herein were developed from a human library and it is expected that the framework regions will not provoke an immune response when administered to humans. Persons of skill can, however, use the information in the art regarding humanizing residues as a guide to make modifications in the framework regions if desired.

Further, since the CDRs of the variable regions determine antibody specificity, the CDRs can be grafted or engineered into an antibody of choice to confer GPNMB-binding specificity upon that antibody. For example, the complementarity determining regions (CDRs), i.e., the antigen binding loops, of the antibodies whose sequences are shown in FIG. 7, or of variants of these antibodies, can be grafted onto a human antibody framework of known three dimensional structure, as known in the art (see, e.g., WO98/45322; WO 87/02671; U.S. Pat. No. 5,859,205; U.S. Pat. No. 5,585,089; U.S. Pat. No. 4,816,567; EP Patent Application 0173494; Jones, et al. *Nature* 321:522 (1986); Verhoeyen, et al., *Science* 239:1534 (1988), Riechmann, et al. *Nature* 332:323 (1988); and Winter & Milstein, *Nature* 349:293 (1991)) to create a GPNMB-binding antibody.

In some embodiments, the light chain and heavy chain of the variable region are joined by a disulfide bond between cysteines engineered into the framework region to form a disulfide-stabilized Fv, or "dsFv." Formation of dsFvs is known in the art, and is taught in, for example, Pastan, U.S. Pat. No. 6,558,672, which is incorporated herein by reference, which sets forth a series of positions at which cysteines can be engineered into the framework region to facilitate formation of disulfide bonding between the chains. In light of the '672 patent, as well as the various disulfide stabilized Fvs that are currently in pre-clinical and clinical trials, the choice of which particular pair of positions to mutate to form the dsFv is considered to be within the skill of the practitioner. In accordance with the '672 patent, in some embodiments, however, the Fv is engineered with a cysteine replacing the residue otherwise present at position 42, 43, 44, 45 or 46 of the light chain, and engineering a cysteine to replace the residue otherwise present at position 103, 104, 105, or 106, of the heavy chain, as the residues of the antibody would be numbered under the Kabat system for numbering antibody residues. On other embodiments, the Fv is engineered to replace the residue otherwise present at 43, 44, 45, 46 or 47 of the heavy chain and mutating a nucleic acid encoding the second variable region so that cysteine is encoded at position 98, 99, 100, or 101 of the light chain (with all positions stated in this paragraph numbered according to the Kabat numbering system).

Methods for manufacturing dsFvs are also known in the art. Typically, the two chains are expressed from separate plasmids in a prokaryotic host cell, such as *E. coli*, and allowed to bond before the protein is purified from the inclusion bodies. Making of dsFvs is exemplified in, for example, Mansfield et al., Blood, 90(5):2020-26 (1997) and FitzGerald et al., International Publication Number WO 98/41641.

In scFv embodiments, the VH and VL chains are expressed as a single fusion protein. In some embodiments, the chains are expressed with the VH chain and the VL chain expressed sequentially without a spacer or linker. More commonly, the two chains are separated by a linker. Conveniently, the linker is a series of glycines separated by a serine residue. To facilitate comparison of the cytotoxicity of the immunotoxins made with the antibodies developed in the course of the studies reported herein, all the immunotoxins were made with the same linker, GGGGSGGGGSGGSA (SEQ ID NO:11). As is evident from the sequence, the linker has two repeats of four glycines followed by a serine (a motif known abbreviated as $G_4S$; SEQ ID NO:45). The linker can be varied, for example, by varying the number of repeats of the $G_4S$ (SEQ ID NO:45) motif, such as by having one, three, four or five repeats of the motif. It will be appreciated, however, that scFvs have been made in the art for well over a decade and that a multitude of other suitable linker peptides are known in the art. The choice of the particular linker to be used with the scFvs of the invention is within the skill of the practitioner and is not critical to the practice of the present invention.

In general, any peptide of about 4 to 20 amino acid residues can be used so long as it does not interfere with the proper folding or activity of the scFv, or of the toxin moiety when the scFv is made into an immunotoxin. The effect of the linker on the activity of the scFv or of the toxin moiety can be readily determined by assaying the binding of the scFv to its target and by assaying the cytotoxicity of the toxic moiety on cells targeted by the scFv. A decrease in binding affinity of the targeting moiety by more than 25% or a decrease in cytotoxicity of the toxin moiety by more than 25%, or both, indicate that the particular linker peptide tested is not suitable. Assays for determining the binding capabilities of numerous antibodies and ligands are known in the art. For example, the binding affinity of a ligand employed as the targeting molecule of the immunotoxin may be assayed by measuring the ability of the targeting molecule to displace a native ligand from its target substrate. This may be accomplished by labeling the native ligand and then incubating cells bearing the target receptor with a fixed amount of the labeled ligand and various concentrations of the ligand-containing immunotoxin. The amount of bound native ligand can be determined by detecting the amount of label bound to the target cell. Unlabeled native ligand can be run as a control.

The improved affinity of the antibodies and antibody fragments provided by the present invention can be incorporated into chimeric immunoconjugates to improve the ability of the chimeric immunoconjugate to target cells bearing the GPNMB antigen. The immunoconjugates can, for example, bear a detectable label such as a radioisotope, a fluorescent moiety, or a reporter enzyme. These labeled immunoconjugates be used, for example, in in vitro assays to detect the presence of GPNMB-expressing cells in a biological sample or can introduced into a patient to permit imaging the location of GPNMB-expressing cells. Once again, the making of immunoconjugates using antibodies and fragments thereof is well known in the art and it is assumed that the person of skill is familiar with the considerable literature on the subject.

In another set of in vitro uses, the immunoconjugate bears a cytotoxin rather than a detectable label. Such immunotoxins can be used to purge GPNMB-expressing cells in a sample from a patient. The cells can then be cultured or used in further studies.

In in vivo uses, immunotoxins made with the antibodies or antibody fragments of the invention can be used to inhibit the growth and proliferation of cancer cells bearing the GPNMB antigen. The high affinity of the antibodies and antibody fragments of the invention and the high cytotoxicity of immunotoxins made with them means that relatively small amounts of the immunotoxins can be administered to achieve a desired therapeutic effect. Since side effects are often dose-dependent, the relatively small amount of immunotoxin that has to be administered to achieve a given therapeutic effect should reduce the occurrence of side effects in patients being administered the immunotoxin and a reduction of the severity of side effects in patients that do experience them.

For ease of comparison, the antibodies of the invention were tested using the same cytotoxin, PE38. As discussed in more detail in the section on cytotoxins below, a number of variants of *Pseudomonas* exotoxin A are known in the art. All share the same mechanism of action and all would be expected be equally potent when used in in vitro uses. PE38 and its variant PE38QQR are somewhat preferred to PE40 for in vivo use against solid tumors since they are somewhat smaller and may permit better penetration of the immunotoxin into the tumor. In addition to PE, other cytotoxins suitable for use in immunotoxins are known in the art and can be used in place of PE38 in creating immunotoxins employing the anti-GPNMB antibodies of the invention.

In some embodiments, the antibody is a scFv or a dsFv. Many of the recombinant immunotoxins produced from constructs of scFv are one-third the size of IgG-toxin chemical conjugates and are homogeneous in composition Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen.

These advantages, however, are offset to some degree by the loss of antigen binding affinity that occurs when IgGs are converted to scFvs (Reiter et al., Nature Biotechnol. 14:239-1245 (1996)). Increasing affinity has been shown to improve selective tumor delivery of scFvs (Adams et al., Cancer Res. 58:485-490 (1998)), and is likely to increase their usefulness in tumor imaging and treatment. Therefore, increasing the affinity of scFvs and other targeting moieties (such as dsFvs, Fabs. and $F(ab')_2$ of immunoconjugates is desirable to improve the efficiency of these agents in delivering effector molecules, such as toxins and other therapeutic agents, to their intended targets. The improved affinity of the antibodies of the invention therefore is an important advance in the delivery of labels and especially toxins to cells of GPNMB-expressing cancers.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Glycoprotein nonmetastatic melanoma protein B, or "GPNMB", refers to a highly glycosylated type I transmembrane protein first discovered a decade ago from a subtractive cDNA library of high and low metastatic human melanoma cell lines. Weterman et al., Int J. Cancer. 60(1):73-81 (1995). The human gpnmb gene encodes a predicted 560-amino acid protein, the deduced amino acid sequence of which shows that GPNMB is made up of three domains: an extracellular domain (464 amino acids) preceded by a signal peptide, a single transmembrane region, and a relatively short cytoplasmic domain composed of 53 amino acid residues. Although the biological function of GPNMB remains to be seen, transfection of a minimally transformed human fetal astrocyte cell line with gpnmb cDNA resulted in a change in the phenotype of the tumor xenografts from minimally invasive to highly invasive and metastatic Persons of skill will recognize that it is the extracellular domain of GPNMB which is the portion exposed on the exterior of the cell and therefore available to be bound by the antibodies and compositions of the invention. Unless otherwise required by context, therefore, references herein to binding GPNMB refer to binding of the extracellular domain of the glycoprotein. For additional specificity, the extracellular domain will occasionally be referred to herein as the GPNMBECD. Human GPNMB exists both in its native form ("GPNMBwt") and a splice variant form in which there is a 12-amino acid in-frame insertion in the extracellular domain ("GPNMBsv").

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE.

The term "antibody fragments" means molecules that comprise a portion of an intact antibody, generally the antigen binding or variable region of the intact antibody.

Examples of antibody fragments include Fab, Fab', $F(ab')_2$, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11):484-490 (2003), Ghahroudi et al., FEBS Lett. 414: 521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

The term "diabodies" refers to small antibody fragments with two antigen-binding sites, which fragments comprise a variable heavy domain ("$V_H$" or "VH") connected to a variable light domain ("$V_L$" or "VL") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., Proc. Natl. Acad. Sci. USA, 90: 6444-6448 (1993).

References to "$V_H$" or a "VH" refer to the variable region of an immunoglobulin heavy chain, including of an Fv, scFv, dsFv or Fab. References to "$V_L$" or a "VL" refer to the variable region of an immunoglobulin light chain, including of an Fv, scFv, dsFv or Fab. The amino acid numbering and CDR delimitation of the G49 antibody was determined according to the IMGT database (Lefranc, M. P., IMGT, the international ImMunoGeneTics database. Nucleic Acids Res, 31(1): 307-10 (2003)). For numbering amino acid residues of the antibodies for preparation of disulfide stabilized antibodies, references to amino acid positions of the heavy or light chains refer to the numbering of the amino acids under the "Kabat" system (Kabat, E., et al., Sequences of Proteins of Immunological Interest, U.S. Government Printing Office, NIH Publication No. 91-3242 (1991). Since the numbering of a residue under the Kabat system aligns it to other antibodies to permit determination of the residues in the framework regions and the CDRs, the number assigned to a residue under the system does not necessarily correspond to the number that one might obtain for a residue in a given heavy or light chain by simply counting from the amino terminus of that chain. Thus, the position of an amino acid residue in a particular VH or VL sequence does not refer to the number of amino acids in a particular sequence, but rather refers to the position as designated with reference to the Kabat numbering scheme.)

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means an antibody of interest which is to be or has been mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

A "targeting moiety" or "targeting portion" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an F(ab')$_2$.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

An antibody immunologically reactive with a particular antigen can be generated by recombinant methods such as selection of libraries of recombinant antibodies in phage or similar vectors, see, e.g., Huse, et al., Science 246:1275-1281 (1989); Ward, et al., Nature 341:544-546 (1989); and Vaughan, et al., Nature Biotech. 14:309-314 (1996), or by immunizing an animal with the antigen or with DNA encoding the antigen.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The term "immunoconjugate" includes reference to a covalent linkage of an effector molecule to an antibody. The effector molecule can be a cytotoxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin A (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W.H. Freeman and Company, New York (2nd Ed., 1992).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. "Chemical means" refers to a reaction between the antibody moiety and the effector molecule such that there is a covalent bond formed between the two molecules to form one molecule, while "recombinant means" refers to expression of a nucleic acid resulting in production of a single, fusion protein which did not first exist as two separate molecules.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, still more preferably over at least about 150 residues and most preferably over the full length of the sequence. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Bioi. 215: 403-410 and Altschuel et al. (1977) Nucleic Acids Res. 25: 3389-3402, respectively. Software for performing BLAST analyses is publicly available on-line through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Nat!. Acad. Sci. USA 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing GPNMB as compared to a cell or tissue lacking GPNMB. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Glycoprotein NMB

The human gpnmb gene encodes a predicted 560-amino acid protein, the deduced amino acid sequence of which shows that GPNMB is made up of three domains, a long extracellular domain (ECD) preceded by a signal peptide, a single transmembrane region, and a relatively short cytoplasmic domain. The human GPNMB amino acid sequence had homology of 71.1% to DC-HIL (Shikano et al., *J Biol Chem*, 276:8125-34 (2001)), 69.8% to Osteoactivin (Safadi et al., *J Cell Biochem*, 84:12-26 (2001)), 56% to the precursor of pMel 17 (Kwon et al., *Proc Natl Acad Sci USA*, 88:9228-32 (1991)), and 51% to QNR-71 (Turque et al., *Embo J*, 15:3338-50 (1996)).

The human GPNMB gene was localized to human chromosome 7q15 (NCBI Unigene Cluster Hs.82226 GPNMB), a locus involved in the human inherited disease cystoid macular dystrophy. Bachner et al suggested that human GPNMB may be a candidate gene for the dominant cystoid macular edema since they found high expression of murine gpnmb mRNA within the retinal and iris pigment epithelium (Bachner et al., *Brain Res Gene Expr Patterns*, 1:159-65 (2002)).

The function of GPNMB has not been fully described, and paradoxical effects have been noted in transfection studies. Transfection of an in vitro minimally transformed human fetal astrocyte line, THRG (Rich et al., *Cancer Res*, 61:3556-60 (2001); Rich et al., *J Biol Chem* (2003)) with gpnmb cDNA altered the phenotype of both subcutaneous and intracranial tumors growing in athymic mice from a minimally invasive to a highly invasive and metastatic phenotype. Conversely, transfection of a partial gpnmb cDNA into a highly metastatic melanoma cell line resulted in slower subcutaneous tumor growth and also in reduction of the potential for spontaneous metastasis in nude mice (Weterman et al., *Int J Cancer*, 60:73-81 (1995)). In studies of high-grade glioma (HGG) biopsy samples by some of the present inventors, gpnmb RNA transcripts were detected in 35/50 GBM (70%), while little or no gpnmb mRNA expression was noted in normal brain samples. By immunohistochemical study of a larger HGG group, 75/108 GBM (70%) were positive for GPNMB protein expression. Furthermore, quantitative flow cytometric analysis of fresh GBM biopsy specimens revealed that cell-surface GPNMB molecular density ranged from 1.1 to $7.8 \times 10^4$ molecules. Its frequent expression in human HGGs and its cell-surface localization make GPNMB a good target for antibody-mediated delivery of cytotoxic agents.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, in some embodiments, the therapeutic agent is a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same effector molecule ("EM") or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LIMB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-GPNMB antibodies can be modified to form the antibodies or immunoconjugates of the present invention. Modification by site-directed mutagenesis is well known in the art. Nucleic acids encoding anti-GPNMB antibodies or immunoconjugates can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-GPNMB scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In more preferred embodiments, cDNA encoding PE is ligated to a scFv so that the toxin is located at the amino terminus of the scFv.

Once the nucleic acids encoding an EM, anti-GPNMB antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-GPNMB antibody, or an immunoconjugate formed using the antibody) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the antibodies and immunoconjugates of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes et al., PROTEIN PURIFICATION: PRINCIPLES AND PRACTICE Springer-Verlag, N.Y. (3rd ed., 1994)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

Cytotoxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin ("DT") is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)).

The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

A. Diphtheria Toxin ("DT")

In some embodiments, the toxin is a mutant form of Diphtheria toxin ("DT"). Most persons in the developed world have been immunized against Diphtheria, which results in the presence of antibodies to DT in the systemic circulation and reduces the utility of DT as the toxic moiety of immunotoxins for systemic administration. Due to the blood-brain barrier, however, anti-DT antibodies do not tend to interfere with the use of DT-based immunotoxins in the brain, and immunotoxin therapy of brain cancers typically involves localized infusion o the tumor or of the area around the tumor after the tumor has been resected. DT-based immunotoxins of the invention are therefore particularly useful for treating gliomas or other brain cancers expressing GPNMB.

DT is a protein secreted by toxigenic strains of *Corynebacterium diphtheriae*. It is initially synthesized as a 535 amino acid polypeptide which undergoes proteolysis to form the toxin, which is composed of two subunits, A and B, joined by a disulfide bond. The B subunit, found at the carboxyl end, is responsible for cell surface binding and translocation; the A subunit, which is present on the amino end, is the catalytic domain, and causes the ADP ribosylation of Elongation Factor 2 ("EF-2"), thereby inactivating EF-2. Since EF-2 is essential for a cell to synthesize proteins, inactivation of the EF-2 in a cell causes its death. See generally, Uchida et al., Science 175:901-903 (1972); Uchida et al., J. Biol. Chem. 248:3838-3844 (1973).

In a preferred series of embodiments, the mutant form of DT is one in which is deficient in the cell binding function but not the cell translocation function. These include mutants in which the native receptor-binding domain, which comprises amino acid residues 384-535, is truncated or wholly removed, and mutants in which one or more residues critical for cell binding or translocation are mutated to residues which reduce or destroy the functionality of the domain. Various deletion mutants of the native receptor-binding domain have been tested in clinical trials, including DT389, a DT in which the carboxyl terminal sequence beginning at residue 389 is removed (e.g., LeMaistre et al., Blood 91:399-405 (1999)), and a form truncated at residue 388. See, Hall et al., Leukemia 13:629-633 (1999). The domain can also be truncated commencing at other residues, such as 385, 386, 387, 390, or 391, or the entire domain, starting at residue 384, can be deleted. Mutants in which smaller portions of the domain are deleted can also be used, provided that they do not retain non-specific binding activity. The degree to which any particular truncation or other mutant retains non-specific binding can be readily measured by standard assays in the art, such as that taught by Vallera et al., Science 222:512-515 (1983).

In a preferred class of embodiments, the mutant DTs contain mutations at one or more residues of the native receptor-binding domain which reduce or eliminate binding of the molecule to the receptor. These include DT molecules which have mutations in the B subunit which result in reduced non-specific binding to cells, such as mutants CRM9, CRM45, CRM102, CRM103, and CRM107, as described, for example, by Nicholls and Youle in Frankel, ed., GENETICALLY ENGINEERED TOXINS, Marcel Dekker, Inc., New York, N.Y. (1992). In a particularly preferred embodiment, the mutated DT is CRM107. CRM107 contains an amino acid substitution of phenylalanine for serine at position 525, resulting in a more than 1000-fold reduction in cell binding, without affecting the translocating properties of the B subunit. The A subunit is unaffected and, when introduced into target cells, retains the full toxicity of native DT. Thus, CRM107 is particularly well suited for use as the toxic moiety, or component, of immunotoxins. It should be noted, however, that position 525 of DT was substituted with each of the natural amino acids and that a number of amino acids were found to result in reduced toxicity to cells (toxicity is usually reduced proportionately to binding of the toxin and can be used as an alternative measure). Thus, while the substitution of phenylalanine for serine resulted in the greatest reduction in toxicity, many of the other amino acid substitutions also reduced toxicity and could be used in the methods herein. Any particular substitution can of course be tested for non-specific toxicity to confirm whether it is suitable for use in the methods of the invention.

Other positions in the native receptor-binding domain can be mutated in place of or addition to position 525 to reduce or eliminate non-specific binding. For examples, position 508 can be mutated from serine to phenylalanine to reduce binding. While this mutation results in the greatest degree of loss of non-specific binding, however, other amino acid residue substitutions also reduce binding. Any particular substitution of another amino acid for the serine at position 508 can be tested to determine the degree to which it has lost the ability to bind non-specifically. Standard assays in the art, such as those taught by Vallera et al., supra, can be used for these determinations. Moreover, one can form a double mutant in which the serine at position 508 and in which the serine at position 525 are both mutated to decrease non-specific binding. In a preferred embodiment, the serine at position 508 and the serine at position 525 are both mutated to phenylalanine.

B. *Pseudomonas* Exotoxin A and its Variants

In preferred embodiments of the present invention, the toxin is *Pseudomonas* exotoxin A ("PE"). Native PE is an extremely active monomeric protein (molecular weight 66 kD), secreted by *Pseudomonas aeruginosa* which inhibits protein synthesis in eukaryotic cells. The native PE sequence is set forth in U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., J Biol Chem 264:14256-61 (1989).

The terms "*Pseudomonas* exotoxin" and "PE" as used herein typically refer to a PE that has been modified from the native protein to reduce or to eliminate non-specific toxicity. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:42) and REDL (SEQ ID NO:43). See, e.g., Siegall, et al., supra. Cytotoxic fragments of PE include those which are cytotoxic with or without subsequent proteolytic or other processing in the target cell (e.g., as a protein or pre-protein). Cytotoxic fragments of PE include PE40, PE38 and its variants PE38QQR and PE38 KDEL, and PE35, as discussed below. In a preferred embodiment, the cytotoxic fragment of PE retains at least 50%, preferably 75%, more preferably at least 90%, and most preferably 95% of the cytotoxicity of native PE. In some preferred embodiments, the cytotoxic fragment is more toxic than native PE.

In preferred embodiments, the PE has been modified to reduce or eliminate non-specific cell binding, frequently by deleting domain Ia. as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E. PE40 is a truncated derivative of PE as previously described in the art. See, Pai, et al., *Proc. Nat'l*

*Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 contains the translocating and ADP ribosylating domains of PE but not the cell-binding portion (Hwang, J. et al., *Cell,* 48:129-136 (1987)). PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)). The sequence of PE38 can be readily determined by the practitioner from the sequence of PE. Persons of skill will be aware that, due to the degeneracy of the genetic code, the amino acid sequence of PE38, of its variants, such as PE38 KDEL (it should be noted that "PE38 KDEL" designates a particular PE38 variant in which the carboxyl terminus ends with the particular residues noted), and of the other PE derivatives discussed herein can be encoded by a great variety of nucleic acid sequences, any of which can be expressed to result in the desired polypeptide.

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK (SEQ ID NO:44)), or may contain a variation found to maintain the ability of the construct to translocate into the cytosol, such as REDL (SEQ ID NO:43) or KDEL (SEQ ID NO:42), and repeats of these sequences. See, e.g., U.S. Pat. Nos. 5,854,044; 5,821,238; and 5,602,095 and WO 99/51643. While in preferred embodiments, the PE is PE38, PE4E, or PE40, any form of PE in which non-specific cytotoxicity has been eliminated or has been reduced to levels in which significant toxicity to non-targeted cells does not occur can be used in the immunotoxins of the present invention so long as it remains capable of translocation and EF-2 ribosylation in a targeted cell.

In preferred embodiments, the PE molecules are further modified to have a substitution of an aliphatic amino acid in place of the arginine normally present at position 490 of the PE molecule. The substitute amino acids can be, for example, G, A, V, L, or I. G, A, and I are more preferred substitutes, with A being the most preferred. Thus, for example, PE40, PE38, PE38 KDEL, PE38QQR, PE4E, PE37, or PE35 can be engineered to have a G, A, or I at position 490 to improve the cytotoxicity of the molecule. In particularly preferred embodiments, the residue at position 490 is changed to an alanine. The PE may also be modified to reduce the immunogenicity of the PE portion of the immunotoxin when used in vivo.

i.) Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

ii.) Assaying for Cytotoxicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing GPNMB on their surface. Thus, an antibody of the present invention, such as an anti-GPNMB scFv, may be attached directly or via a linker to a drug that is to be delivered directly to cells bearing GPNMB. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-GPNMB antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985).

Detectable Labels

The high affinity of the antibodies of the present invention also makes them suitable as improved reagents for labeling GPNMB-expressing cells. Antibodies used for these purposes may be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Conjugation of Toxins or Labels to the Antibody

In a non-recombinant embodiment of the invention, effector molecules, e.g., therapeutic, diagnostic, or detection moieties, are linked to the anti-GPNMB antibodies of the present invention using any number of means known to those of skill in the art. Both covalent and noncovalent attachment means may be used with anti-GPNMB antibodies of the present invention.

The procedure for attaching an effector molecule to an antibody will vary according to the chemical structure of the EM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Pharmaceutical Compositions and Administration

The antibody and/or immunoconjugate compositions of this invention (i.e., PE linked to an anti-GPNMB antibody of the invention) are useful for localized administration, such as administration into the brain, or parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

For administration of immunoconjugates of the invention, such as an immunotoxin, directly into the brain or directly into a brain tumor can be performed by techniques conventional in neurosurgery, including stereotactic cannulation and visual observation followed by direct injection into sites around the site from which a tumor has been excised to kill residual cells. High-flow interstitial microinfusion of immunotoxins to treat brain cancers is described in detail, for example, in Laske, D. W. et al., Nat. Med., 3:1362-1368 (1997). Convection-enhanced delivery, in which a pressure gradient is used to distribute immunotoxins in the brain is described in, for example, Kunwar, Acta Neurochir Suppl. 88:105-11 (2003). Clinical trials administering DT-based and PE-based immunotoxins to brain tumors have been conducted at hospitals around the United States. See, e.g., Weaver and Laske, J. Neurooncol. 65(1):3-13 (2003); and Husain and Puri, J. Neurooncol. 65(1):37-48 (2003).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is to inhibit the growth of malignant cells expressing GPNMB. Exemplary malignant cells include those of GPNMB-expressing gliomas and melanomas.

Diagnostic Kits and In Vitro Uses

In another embodiment, this invention provides for kits for the detection of GPNMB or an immunoreactive fragment thereof, (i.e., collectively, a "GPNMB protein") in a biological sample. A "biological sample" as used herein is a sample of biological tissue or fluid. Such samples include, but are not limited to, tissue from biopsy, blood, or other biological fluids containing cells. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

Kits will typically comprise an anti-GPNMB antibody of the present invention. In some embodiments, the anti-GPNMB antibody will be an anti-GPNMB Fv fragment, such as a scFv or dsFv.

In addition the kits will typically include instructional materials disclosing means of use of an antibody of the present invention (e.g. for detection of glioma cells or melanoma cells in a biopsy sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting GPNMB in a biological sample generally comprises the steps of contacting the biological sample with an antibody of the present invention which specifically reacts, under immunologically reactive conditions, to GPNMB. The antibody is allowed to bind to GPNMB under immunologically reactive conditions, and the presence of the bound antibody is detected directly or indirectly.

Due to the increased affinity of the antibodies of the invention, the antibodies will be especially useful as diagnostic agents and in in vitro assays to detect the presence of GPNMB in biological samples. For example, the antibodies taught herein can be used as the targeting moieties of immunoconjugates in immunohistochemical assays to determine whether a sample contains cells expressing GPNMB. Detection of GPNMB in lymphocytes would indicate either that the patient has a cancer characterized by the presence of GPNMB-expressing cells, or that a treatment for such a cancer has not yet been successful at eradicating the cancer.

In another set of uses for the invention, immunotoxins targeted by antibodies of the invention can be used to purge targeted cells from a population of cells in a culture. Thus, for example, cells cultured from a patient having a cancer expressing GPNMB can be purged of cancer cells by contacting the culture with immunotoxins which use the antibodies of the invention as a targeting moiety.

EXAMPLES

The following examples are offered to illustrate, but not to limit the claimed invention.

Example 1

Isolation of Anti-GPNMB scFv G49

Library and Panning

To obtain GPNMB-specific scFv, a human synthetic phage display library of $1.2 \times 10^9$ members (Griffin.1 library from MRC Center for Protein Engineering, Cambridge, UK) was panned on recombinant protein GPNMB$_{ECD}$ defining the extracellular domain ("ECD") of GPNMB (Weterman et al., *Int J Cancer*, 60:73-81 (1995)). GPNMB$_{ECD}$ protein was produced in High Five™ insect cells (Invitrogen Corp., Carlsbad, Calif.) and biotinylated for use as a target antigen in panning procedure.

Panning was carried out in a solution according to the method described previously (Amersdorfer, P. and Marks, J. D., *Methods Mol Biol;* 145:219-40 (2000)). After four rounds of panning, 12 phage clones were randomly selected to test the reactivity with GPNMB$_{ECD}$. 9 of 12 were positive by phage ELISA and DNA fingerprinting and sequencing revealed that all 9 clones had identical scFv sequence. This clone was designated as G49 (Table 1).

G49 scFv Antibody and BIACore Analysis

Figure 1:
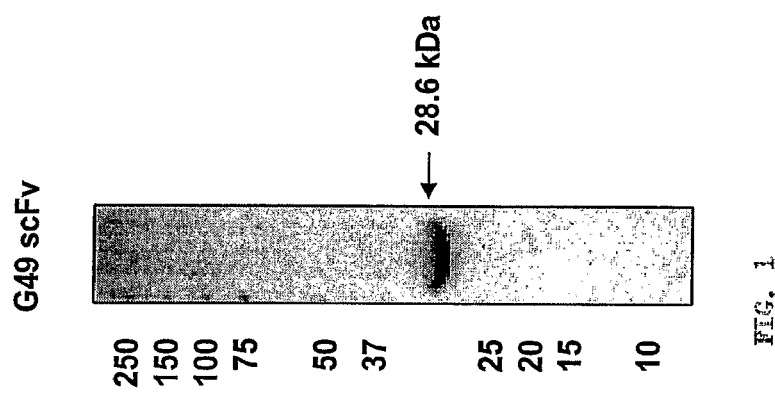
FIG. 1 is a photograph of an SDS-PAGE gel of electrophoresed G49 scFv antibody. Five μg of G49 scFv (28.6 kD, indicated by an arrow) was electrophoresed through 4-12%

To generate G49 scFv antibody, DNA fragment encoding G49 scFv was excised from the corresponding phagemid by NcoI and NotI digestion and ligated into the NcoI-NotI sites of the pET22 vector (Novagen, Madison, Wis.), in which scFv protein is tagged at the carboxy terminus with hexahistidine and myc sequences for purification and detection. Plasmids were introduced to *E. coli* BL21(DE3) Gold cells (Stratagene, La Jolla, Calif.). His-tagged G49 scFv antibody was expressed and purified using metal affinity resin (BD TALON™, BD Biosciences, Palo Alto, Calif.) according to the manufacturer's instruction (FIG. 1).

Binding affinity of purified G49 scFv antibody was measured by surface plasmon resonance (BIACore analysis, BIAcore Inc, Piscataway, N.J.). G49 scFv antibody had a $K_D$ of 8.4 nM for GPNMB$_{ECD}$ protein (Table 2).

G49-PE38 Immunotoxin and Cytotoxicity Assay

Recombinant immunotoxin G49-PE38 was constructed by fusing G49 scFv to the sequences for domains II and III of *Pseudomonas* exotoxin A (Beers et al., *Clin Cancer Res;* 6:2835-43. (2000)) (FIG. 2). In the refolding process of immunotoxin, 50 mg of soluble G49-PE38 was obtained from 300 mg of solubilized inclusion bodies, giving a yield of about 17%. By BIACore analysis, purified G49-PE38 immunotoxin had a $K_D$ of 3.2 nM for GPNMB$_{ECD}$ protein (Table 2).

Immunotoxin G49-PE38 was used in cytotoxicity assays on GPNMB-expressing glioma cells. D392 MG and D54 MG cells are glioblastoma-derived cell lines. (Bigner, D. et al., *J Neuropathol Exp Neurol* 40(3): 201-29 (1981)). D392 MG glioma cells that express 2.5×10$^5$ surface GPNMB molecules per cell defined by quantitative FACS analysis were chosen as a target. G49-PE38 immunotoxin inhibited 50% of protein synthesis at a concentration of 23 ng/ml on D392 MG cells when the cells were exposed to immunotoxin for 20 h, while control anti-Tac(Fv) PE40 immunotoxin did not show cytotoxic activity at up to 1000 ng/ml (FIG. 3). No cytotoxicity was noted on GPNMB-negative cell lines, including HEK293, A431 and mouse fibroblast NR6 cells, at concentration up to 1000 ng/ml, indicating that the cytotoxicity of G49-PE38 is restricted to GPNMB-expressing cells.

Example 2

Affinity Maturation of GPNMB-Binding scFv G49

To obtain mutants of G49 with an increased affinity for GPNMB, random complementarity determining region (CDR) mutagenesis was carried out.

Light Chain CDR3 Mutagenesis

CDR3 of the light chain of G49 clone consists of 9 amino acids containing one consensus hot spot sequence (Table 3). $V_L$CDR3 was mutated using degenerate oligonucleotide PCR primers each randomizing three consecutive amino acids (FIG. 4 and Table 4). Three $V_L$ libraries, L1 for residue 1-3, L2 for residue 4-6, and L3 for residue 7-9 random mutagenesis, were constructed in pCANTAB5E phagemid system as described previously (Weterman et al., *Int J Cancer,* 60:73-81 (1995)). After transformation of *E. coli* TG1, each library contained approximately 1.0×10$^6$ clones.

Cell-based palming was performed using GPNMB-expressing glioma cell line D54 MG as a target (Weterman et al., *Int J Cancer,* 60:73-81 (1995)). 2×10$^7$ D54 MG cells, maintained in zinc option medium supplemented with 10% FBS, were harvested using 0.02% EDTA and suspended in 10 ml of Dulbecco's PBS containing 2% BSA. 1×10$^{10}$ pfu phages from each light chain CRD3 library were combined (3×10$^{10}$ pfu phages in total) and added to D54 MG cell suspension. The mixture was rotated at 4° C. for 2 h. Then, cells were washed with 10 ml of 2% BSA/Dulbecco's PBS three times and bound phages were eluted in ice-cold 50 mM HCl and neutralized. Half of the eluted phages were amplified for use in the next round of selection.

After three rounds of panning, 24 clones were selected randomly and subjected to phage rescue to assess their ability to bind to GPNMB. By phage ELISA, 19/24 clones were positive for GPNMB and 14 clones that had ELISA signal stronger than that of parental G49 phage were processed for DNA sequencing (FIG. 5). All these 14 clones except for one clone identical to parental G49 belonged to library L1 and had amino acid substitution in hot spot position (Table 4).

Heavy Chain CDR3 Mutagenesis

G49 heavy chain CDR3 consists of 4 amino acids and contains no hot spot sequence (Table 3). A $V_H$CDR3 library was constructed by mutating all these four amino acids simultaneously (FIG. 4) and palming was carried out as described for $V_L$CDR3 library. After three rounds of selection, 11/24 clones were positive for GPNMB by phage ELISA. However, DNA sequencing revealed that all 11 clones were identical to the parental G49 scFv.

Cytotoxicity Assay of Selected Mutants

Three of the 14 mutants (L22, L04 and L12) that had the strongest ELISA signal were used to construct immunotoxin and purified immunotoxins were assayed for their cytotoxicity on D392 MG and D54 MG cells. Compared with the parental clone G49-PE38, one mutant clone, L22-PE38 (Gln→Glu and Ala→Thr), exhibited improved cell-killing activity toward D392 MG and D54 MG by several fold (Table 5, FIG. 6). There was no cytotoxic activity of L22-PE38 on GPNMB-negative HEK293, A431, or NR6 cells (FIG. 6).

Conclusion:

G49 and L22 anti-GPNMB scFv immunotoxins were successfully produced and showed good cytotoxic activity to various GPNMB-positive cell lines but not to GPNMB-negative lines.

Example 3

Development of Mutants of L22 with Yet Higher Affinity and Cytotoxicity when Made into Immunotoxins In addition to the hot spot affinity maturation studies discussed above, hot spot affinity maturation studies were conducted in which the VH and VL CDRs 1 and 2 of the L22 antibody sequence were mutated. Thus, the VH CDR1 and 2 and VL CDR1 and 2 were subjected to hot spot mutatagenesis. Only mutations in two residues of VH CDR1 resulted in mutants with higher affinity than the starting, L22, antibody. These clones, designated B307 and 902V, both were tested as immunotoxins and both resulted in immunotoxins with surprisingly better cytotoxicity than that of like immunotoxins made with G49 or the L22 antibody. By DNA sequencing of plasmids rescued from yeast cells, B307 was found to have a single substitution of G instead of S at position 31 in the VH CDR1 domain. (See Table 7). Co-incubation with 50-fold molar excess of GPNMBECD protein abrogated the cytotoxicity of B307-PE38 on D54 MG cells, indicating that the cell-killing activity of anti-GPNMB toxin observed is dependent on the specific interaction of the antibody with the cell surface target molecule.

The results of the studies of the affinity of the G49, L22, B307 and 902V antibodies, and the results of studies comparing the cytotoxicity of immunotoxins using the antibodies as the targeting portion of the immunotoxin are set forth in Table 5. The cytotoxicities shown as IC50 values reflect the amount of immunotoxin found to inhibit protein synthesis by 50% when cells were exposed to immunotoxin for 24 hours. To ensure the comparison was meaningful, all of the immunotoxins were made using the same linker between the targeting antibody and the cytotoxin, and all the immunotoxins were made with the same toxin. It is expected that similar comparative results would obtain with different linkers and with different toxins. As shown in Table 5, when converted to an immunotoxin form, B307-PE38 exhibited 3- and 5-fold improvement in cytotoxic activity on D392 MG and D54 MG cells, respectively, compared to a like immunotoxin made with L22, while 902V-PE38 exhibited double the cytotoxicity of B307-PE38 on D392MG cells and triple the cytotoxicity of B307-PE38 on D54MG cells. Similar studies were conducted on immunotoxins made with antibodies 201, B308, B305, L04, L12, and L15. The results are shown in Tables 8 and 9, respectively.

Accordingly, the anti-GPNMB antibodies of the invention are expected to form potent targeting moieties for directing immunoconjugates, including toxin moieties, to GPNMB-expressing cells.

TABLE 1

Panning of Human Synthetic Phage Display Library for GPNMB-specific scFv.

| Round | Number of Phage Panned (pfu) | Antigen Concentration (nM) | Number of Phage Eluted (pfu) | Incidence of GPNMB-binding Clone G49[a] |
|---|---|---|---|---|
| 1 | $3.7 \times 10^{13}$ | 500 | $5.2 \times 10^{6}$ | 0/12 (0%) |
| 2 | $1.0 \times 10^{12}$ | 100 | $3.1 \times 10^{3}$ | 0/12 (0%) |
| 3 | $1.0 \times 10^{12}$ | 20 | $1.2 \times 10^{6}$ | 5/12 (42%) |
| 4 | $1.0 \times 10^{12}$ | 4 | $1.1 \times 10^{7}$ | 9/12 (75%) |

[a]Determined by DNA fingerprinting and sequencing.

TABLE 2

BIACore Analysis of G49 scFv Antibody and G49-PE38 immunotoxin

| | $k_{assoc}$ (1/Ms) | $k_{dissoc}$ (1/S) | $K_A$ (1/M) | $K_D$ (M) |
|---|---|---|---|---|
| G49 scFv | $9.5 \times 10^{3}$ | $8.0 \times 10^{-5}$ | $1.2 \times 10^{8}$ | $8.4 \times 10^{-9}$ |
| G49-PE38 | $9.0 \times 10^{3}$ | $8.3 \times 10^{-5}$ | $1.1 \times 10^{8}$ | $9.1 \times 10^{-9}$ |

TABLE 3

DNA and Amino Acid Sequence of Light-Chain CDR3 and Heavy-Chain CDR3 of G49 scFv G49 (VL CDR3) (DNA) (SEQ ID NO.: ID NO: 46)   ATG CA<u>A</u> <u>GCT</u> CTA CAA ACT CAC CCT ACG G49 (VL CDR3) (Amino acid) (SEQ ID NO: 33)   M Q A L Q T H P T

G49 (VH CDR3) (DNA) (SEQ ID NO: 47)   GGG CCT AAT ACG

G49 (VH CDR3) (Amino acid) (SEQ ID NO: 30)   G P N T

Hot spot with the sequence Pu-G-Py-A/T is underlined.

TABLE 4

Sequence of Mutant Phage Isolated from Light Chain CDR3 Library

Parental clone G49

(residue) 1 2 3 4 5 6 7 8 9

M Q A L Q T H P T

VL CDR3 libraries

L1 library X X X L Q T H P T  (SEQ ID NO: 48)
L2 library M Q A X X X H P T  (SEQ ID NO: 49)
L3 library M Q A L Q T X X X  (SEQ ID NO: 50)

| Mutant | | | | | | | | | | Incidence in 24 clones (SEQ ID NO:) |
|---|---|---|---|---|---|---|---|---|---|---|
| L22 | M | E | T | L | Q | T | H | P | T | 1 (34) |
| L04 | E | P | T | L | Q | T | H | P | T | 1 (35) |
| L12 | A | M | T | L | Q | T | H | P | T | 1 (36) |
| L15 | G | V | A | L | Q | T | H | P | T | 1 (37) |
| L21 | L | P | T | L | Q | T | H | P | T | 1 (51) |
| L16 | G | P | T | L | Q | T | H | P | T | 2 (52) |
| L08 | A | V | A | L | Q | T | H | P | T | 1 (53) |
| L24 | G | L | A | L | Q | T | H | P | T | 1 (54) |
| L20 | G | L | T | L | Q | T | H | P | T | 1 (55) |
| L18 | V | M | T | L | Q | T | H | P | T | 1 (56) |
| L07 | H | M | S | L | Q | T | H | P | | 1 (57) |
| L10 | M | Q | A | L | Q | T | H | P | T | 1 (33; identical to G49) |
| L11 | E | R | W | L | Q | T | H | P | T | 1 (58) |

Mutated residues are indicated in bold.

TABLE 5

Binding Affinity and Cytotoxic Activity (IC$_{50}$) in ng/ml of Anti-GPNMB Immunotoxins ("IT") on GPNMB+ and GPNMB− (control) cells

| Immuno-toxin | CDRs of G49 Mutated | Affinity ($K_D$) | D392 MG (IC$_{50}$ of IT in ng/ml) | D54 MG (IC$_{50}$ of IT in ng/ml) | HEK293 (IC$_{50}$ of IT in ng/ml) |
|---|---|---|---|---|---|
| G49-PE38 | | 9.1 nM | 30 | 100 | >1000 |
| L22-PE38 | V$_L$ CDR3 | 3.7 nM | 6 | 30 | >1000 |
| B307-PE38 | V$_L$ CDR3 + V$_H$ CDR1 | 2.9 nM | 2 | 6 | >1000 |
| 902V-PE38 | V$_L$ CDR3 + V$_H$ CDR1 | 0.77 nM | 1 | 2 | >1000 |

D392 MG and D54 MG are GPNMB+ cell lines, HEK293 cells are GPNMB− cells used as controls.

TABLE 6

Yields of Anti-GPNMB Immunotoxins

| Clone | Scale | Inclusion Body | Immunotoxin | |
|---|---|---|---|---|
| G49 | 3 L | 300 mg (50 mg/L) | 15.4 mg (1.4 mg/L) | 5.1% |
| L22 | 3 L | 260 mg (86.6 mg/L) | 14.4 mg (4.8 mg/L) | 5.5% |
| B307 | 3 L | 90 mg (45 mg/L) | 3.9 mg (1.95 mg/L) | 4.3% |
| 902V | 2 L | 127 mg (63.5 mg/L) | 4.7 mg (2.35 mg/L) | 3.7% |

TABLE 7

Amino Acid Differences in VH CDR1 and VL CDR3 of Anti-GPNMB Immunotoxins

| Clone No. | VH CDR1 | VL CDR3 | SEQ ID NOS:*/ for VH: | SEQ ID NOS:*/ for VL: |
|---|---|---|---|---|
| G49 | S S Y | M A Q | 1 | 6 |
| L22 | S S Y | M E T | 2 | 7 |
| B307 | G S Y | M E T | 3 | 8 |
| 902V | G T Y | M E T | 4 | 9 |

TABLE 8

V$_H$ CDR1 MUTANTS

| Clone[e)] | Position[b)] 31 | 32 | 33 | $K_D$ (nM)[c)] | IC$_{50}$ (ng/ml)[d)] |
|---|---|---|---|---|---|
| L22 (parental) | S | S | Y | 3.7 | 6 |
| 902V | G | T | Y | ND | 1 |
| B307 | G | S | Y | 1.0 | 2 |
| 201[e)] | A | R | T | 3.0 | 4 |
| B308 | S | R | T | ND | 6 |
| B305[e)] | S | T | T | ND | 6 |

[a)] Five mutant clones that had mean fluorescent intensity in flow cytometry higher than the cells expressing parental clone L22.
[b)] Amino acid numbering determined by IMAT and refers to the first three positions of the VH CDR1, as shown in FIG. 7.
[c)] Determined by BIACore on the corresponding immunotoxins.
[d)] Determined by cytotoxicity assay using antibody-PE38 immunotoxin on D392 MG cells.
[e)] Clones were selected by yeast surface display and flow cytometry.
ND; Not determined.

TABLE 9

BIOPANNING OF V$_L$ CDR3 MUTANT LIBRARY BY PHAGE DISPLAY; SEQUENCE, BINDING AFFINITY, AND CYTOTOXIC ACTIVITY OF MUTANT SCFVS AND IMMUNOTOXINS.

| Clone[a)] | Position[b)] 105 | 106 | 107 | $K_D$ (nM)[c)] | IC$_{50}$ (ng/ml)[d)] |
|---|---|---|---|---|---|
| G49 (parental) | M | Q | A | 8.4 | 30 |
| L22 | M | E | T | 3.7 | 6 |
| L04 | E | P | T | | 15 |
| L12 | A | M | T | | 20 |
| L15 | G | V | A | | 30 |
| L21 | L | P | T | ND | ND |
| L16 | G | P | T | ND | ND |

[a)] Six mutant clones that had phage ELISA signals higher than 3-fold increase over the parental G49 phage.
[b)] Amino acid numbering determined by IMAT.
[c)] Determined by BIACore using corresponding immunotoxin.
[d)] Determined by cytotoxicity assay of antibody-PE38 on D392 MG cells.
ND; Not determined due to low yield of immunotoxin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

We claim:

1. An isolated nucleic acid encoding a polypeptide comprising an antibody heavy chain variable region ("VH") and an antibody light chain variable region ("VL"), each variable region having an amino terminus and a carboxyl terminus and comprising four framework regions ("FRs"), which FRs of each variable region are numbered sequentially FRs 1-4 starting from the amino terminus, and three complementarity determining regions ("CDRs"), which CDRs of each variable region are numbered sequentially CDR1 to CDR3 starting from the amino terminus, wherein CDR1 of said VH has a sequence selected from the group consisting of SEQ ID NOs: 22-28, CDR2 of said VH has the sequence of SEQ ID NO:29, CDR3 of said VH has the sequence of SEQ ID NO:30, CDR1 of said VL has the sequence of SEQ ID NO:31, CDR2 of said VL has the sequence of SEQ ID NO:32, and CDR3 of said VL has a sequence selected from the group consisting of SEQ ID NO:33-37, wherein the polypeptide binds specifically to human glycoprotein NMB (GPNMB).

2. The isolated nucleic acid of claim 1, wherein said CDR1 of said VH of said polypeptide has the sequence of SEQ ID NO:23 and said CDR3 of said VL of said polypeptide has the sequence of SEQ ID NO:34.

3. The isolated nucleic acid of claim 1, wherein said CDR1 of said VH of said polypeptide has the sequence of SEQ ID NO:24 and said CDR3 of said VL of said polypeptide has the sequence of SEQ ID NO:34.

4. The isolated nucleic acid of claim 1, wherein said CDR1 of said VH of said polypeptide has the sequence of SEQ ID NO:25 and said CDR3 of said VL of said polypeptide has the sequence of SEQ ID NO:34.

5. The isolated nucleic acid of claim 1, wherein said CDR1 of said VH of said polypeptide has the sequence of SEQ ID NO:26 and said CDR3 of said VL of said polypeptide has the sequence of SEQ ID NO: 34.

6. The isolated nucleic acid of claim 1, wherein said FRs 1, respectively, of said VH of said polypeptide have the sequence of FRs 1-4, respectively, of the VH of antibody G49 as shown in SEQ ID NO:1 and wherein said FRs 1-4, respectively, of said VL have the sequence of FRs 1-4, respectively, of the VL of antibody G49 as shown in SEQ ID NO:1.

7. The isolated nucleic acid of claim 1, further encoding an effector moiety fused to said polypeptide.

8. The isolated nucleic acid of claim 7, wherein said effector moiety is a cytotoxin.

9. The isolated nucleic acid of claim 8, wherein said cytotoxin is a *Pseudomonas* exotoxin A ("PE").

* * * * *